(12) United States Patent
Wang et al.

(10) Patent No.: US 9,313,423 B2
(45) Date of Patent: Apr. 12, 2016

(54) DEEP TISSUE FOCAL FLUORESCENCE IMAGING WITH DIGITALLY TIME-REVERSED ULTRASOUND-ENCODED LIGHT

(71) Applicants: California Institute of Technology, Pasadena, CA (US); Northeastern University, Boston, MA (US)

(72) Inventors: Ying Min Wang, Pasadena, CA (US); Benjamin Judkewitz, Los Angeles, CA (US); Charles A. DiMarzio, Cambridge, MA (US); Changhuei Yang, Alhambra, CA (US)

(73) Assignees: California Institute of Technology, Pasadena, CA (US); Northeastern University, Boston, MA (US); London School of Hygiene & Tropical Medicine, London (GB)

( * ) Notice: Subject to any disclaimer, the term of this patent is extended or adjusted under 35 U.S.C. 154(b) by 304 days.

(21) Appl. No.: 13/851,901

(22) Filed: Mar. 27, 2013

(65) Prior Publication Data

US 2013/0342665 A1    Dec. 26, 2013

Related U.S. Application Data

(60) Provisional application No. 61/616,347, filed on Mar. 27, 2012.

(51) Int. Cl.
*G02F 1/11* (2006.01)
*H04N 5/30* (2006.01)
*A61N 5/00* (2006.01)
*G01N 27/447* (2006.01)

(52) U.S. Cl.
CPC .. *H04N 5/30* (2013.01); *G02F 1/11* (2013.01); *A61N 5/00* (2013.01); *G01N 27/44721* (2013.01)

(58) Field of Classification Search
CPC .......................................................... H04N 5/30
USPC .......................................................... 348/61
See application file for complete search history.

(56) References Cited

U.S. PATENT DOCUMENTS

| 8,450,674 | B2* | 5/2013 | Yang | G02B 21/0056 250/208.1 |
|---|---|---|---|---|
| 2011/0108707 | A1* | 5/2011 | Cui | G02B 21/0056 250/208.1 |
| 2011/0309267 | A1* | 12/2011 | Cui | H05K 999/00 250/492.1 |
| 2014/0118739 | A1* | 5/2014 | Judkewitz | G01N 21/49 356/338 |

OTHER PUBLICATIONS

Atlan, M., et al., "Pulsed acousto-optic imaging in dynamic scattering media with heterodyne parallel speckle detection", Optics Letters, vol. 30, No. 11, Jun. 1, 2005, pp. 1360-1362.

(Continued)

*Primary Examiner* — Richard Torrente
*Assistant Examiner* — Marnie Matt
(74) *Attorney, Agent, or Firm* — Gates & Cooper LLP

(57) ABSTRACT

A device and method for performing fluorescence imaging with digitally time reversed ultrasound encoded light, using a source of ultrasound waves, a coherent light source, a digital optical phase conjugation (DOPC) device comprising a camera and a spatial light modulator (SLM), a detector of fluorescence, and one or more computers, to obtain an output that at least approximates an interaction between a complete time reversed field, of all of the encoded light's fields, and the scattering medium.

22 Claims, 16 Drawing Sheets

$E_{sc}$, input (scattered field)

(56) References Cited

OTHER PUBLICATIONS

Conkey, D.B., et al., "High-speed scattering medium characterization with application to focusing light through turbid media", Optics Express, vol. 20, No. 2, pp. 1733-1740, Jan. 16, 2012.
Cui, M., et al., "An in vivo study of turbidity suppression by optical phase conjugation (TSOPC) on rabbit ear", Optics Express, vol. 18, No. 1, pp. 25-30, Jan. 4, 2010.
Cui, M., et al., "Implementation of a digital optical phase conjugation system and its application to study the robustness of turbidity suppression by phase conjugation", Optics Express, vol. 18, No. 4, pp. 3444-3455, Feb. 15, 2010.
Denk, W., et al., "Two-Photon Laser Scanning Fluorescence Microscopy", Science 248, pp. 73-76, Apr. 6, 1990.
Feinberg, J., et al., "Phase-conjugating mirror with continuous-wave gain", Optics Letters, vol. 5, No. 12, pp. 519-521, Dec. 1980.
Feinberg, J., et al., "Photorefractive effects and light-induced charge migration in barium titanate", Journal of Applied Physics 51(3), pp. 1297-1305, Mar. 1980.
Goodman, J. W., et al., "Wavefront-Reconstruction Imaging Through Random Media", Applied Physics Letters, vol. 8, pp. 311-313, Jun. 15, 1966.
Gross, M., et al., "Detection of the tagged or untagged photons in acousto-optic imaging of thick highly scattering media by photorefractive adaptive holography", The European Physical Journal E 28, pp. 173-182 (2009).
Gu, C., et al., "Partial phase conjugation, fidelity, and reciprocity", Optics Communications 107, pp. 353-357, May 1, 1994.
Helmchen, F., et al., "Deep tissue two-photon microscopy", Nat. Meth., vol. 2, No. 12, pp. 932-940, Dec. 2005.
Hsieh, C.L., et al., "Digital phase conjugation of second harmonic radiation emitted by nanoparticles in turbid media", Optics Express, vol. 18, No. 12, pp. 12283-12290, Jun. 7, 2010.
Huang, D., et al., "Optical coherence tomography", Science, New Series, vol. 254, No. 5035, Nov. 22, 1991, pp. 1178-1181.
Katz, O., et al., "Focusing and compression of ultrashort pulses through scattering media", Nature Photonics, vol. 5, pp. 372-377, Jun. 2011.
Kothapalli, S.-R., et al., "Ultrasound-modulated optical microscopy", Journal of Biomedical Optics 13(5), 054046 (Sep./Oct. 2008).
Lai, P., et al., "Reflection-mode time-reversed ultrasonically encoded optical focusing into turbid media", Journal of Biomedical Optics, vol. 16(8), 080505, Aug. 2011.
Leith, E. N., et al., "Holographic Imagery Through Diffusing Media", Journal of the Optical Society of America, vol. 56, No. 4, p. 523, Apr. 1966.
Leray, A. et al., "Enhanced Background Rejection in Thick Tissue with Differential-Aberration Two-Photon Microscopy", Biophysical Journal, vol. 94, pp. 1449-1458, Feb. 2008.
Lev, A. et al., "In vivo demonstration of the ultrasound-modulated light technique", Journal of the Optical Society of America, Electro-Optics Division, NRC Soreq, Yavne 81800, Israel, vol. 20, No. 12, pp. 2347-2354, Dec. 2003.
Li, Y. et al "Detection of ultrasound-modulated diffuse photons using spectral-hole burning", Optics Express, vol. 16, No. 19, pp. 14862-14874, Sep. 15, 2008.
Liu, H., et al., "Time-reversed ultrasonically encoded optical focusing into tissue-mimicking media with thickness up to 70 mean free paths", Journal of Biomedical Optics, vol. 16(8), 086009, Aug. 2011.
McCabe, D. J., et al., "Spatio-temporal focusing of an ultrafast pulse through a multiply scattering medium", Nature Communications 2:447, Aug. 23, 2011.
McDowell, E. J. et al., "Turbidity suppression from the ballistic to the diffusive regime in biological tissues using optical phase conjugation", Journal of Biomedical Optics, vol. 15(2), 025004, Mar./Apr. 2010.
Ntziachristos, V., et al., "Looking and listening to light: the evolution of whole-body photonic imaging", Nature Biotechnology, vol. 23, No. 3, pp. 313-320, Mar. 2005.
Ntziachristos, V., "Going deeper than microscopy: the optical imaging frontier in biology", Nature Methods, vol. 7, No. 8, pp. 603-614, Aug. 2010.
Popoff, S., et al., "Image Transmission Through an Opaque Material", Optical Society of America, Sep. 23, 2010.
Si, Ke, et al., "Fluorescence imaging beyond the ballistic regime by ultrasound-pulse-guided digital phase conjugation", Nature Photonics, Letters, vol. 6, Oct. 2012, pp. 657-661.
Van Putten, E.G., et al., "Scattering Lens Resolves Sub-100 nm Structures with Visible Light", Physical Review Letters 106, 193905 (2011) American Physical Society.
Vellekoop, I. M., et al., "Focusing coherent light through opaque strongly scattering media", Optics Letters, vol. 32, No. 16, pp. 2309-2311, Aug. 15, 2007.
Vellekoop, I. M., "Controlling the Propagation of Light in Disordered Scattering Media", University of Twente Thesis, pp. 1-142 (2008).
Vellekoop, I. M., et al., "Universal Optimal Transmission of Light Through Disordered Materials", Physical Review Letters 101, 120601, The American Physical Society (2008).
Vellekoop, I. M., et al., "Exploiting disorder for perfect focusing", Nature Photonics 4, pp. 320-322, Feb. 14, 2010.
Xu, Xiao, et al., "Time-reversed ultrasonically encoded optical focusing into scattering media", Nature Photonics, Letters, vol. 5, Mar. 2011, pp. 154-157.
Yamaguchi, I., et al., "Phase-shifting digital holography", Optics Letters, vol. 22, No. 16, Aug. 15, 1997, pp. 1268-1270.
Yaqoob, Z., et al., "Optical phase conjugation for turbidity suppression in biological samples", Nature Photonics, vol. 2, pp. 110-115, Feb. 2008.
Yariv, A., "Phase Conjugate Optics and Real-Time Holography", IEEE Journal of Quantum Electronics, vol. QE-14, No. 9, Sep. 1978, pp. 650-660.
Zawadzki, R. J., et al., "Adaptive-optics optical coherence tomography for high-resolution and high-speed 3D retinal in vivo imaging", Optics Express, vol. 13, No. 21, pp. 8532-8546, Oct. 17, 2005.
"PLUTO Phase Only Spatial Light Modulator (Reflective)", last accessed Oct. 9, 2014, http://holoeye.com/spatial-light-modulators/slm-pluto-phase-only/.
http://www.pco.de/categories/scmos-cameras/pcoedge/, accessed via Internet Archive WayBackMachine dated Mar. 8, 2013.
Olympus, High Frequency V3330, last accessed Oct. 9, 2014, http://shop.olympus-ims.com/en/shop/item/269productld.570437674_269-catId.562036984.html.
Reference 57 from the Specification of the Application, by Wang, Y. M., B. Judkewitz, et al. (2012). Nat Commun 3: 928; DOI 10:1038/ncomms1925, entitled "Deep-tissue focal fluorescence imaging with digitally time-reversed ultrasound-encoded light."

* cited by examiner

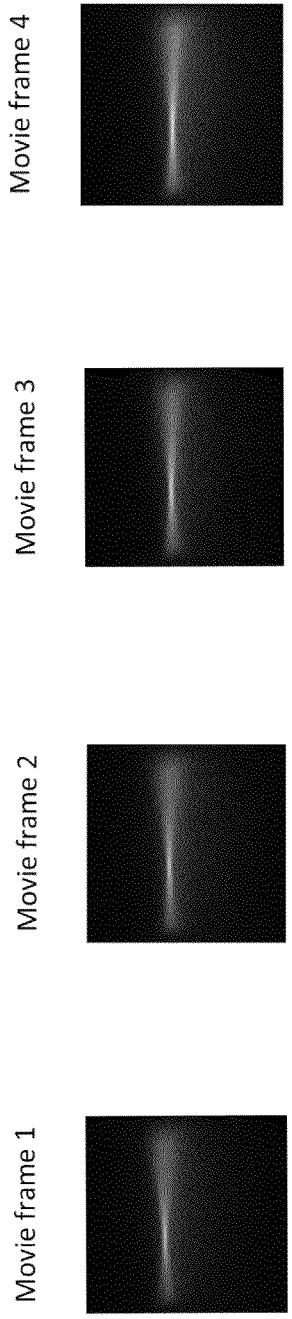
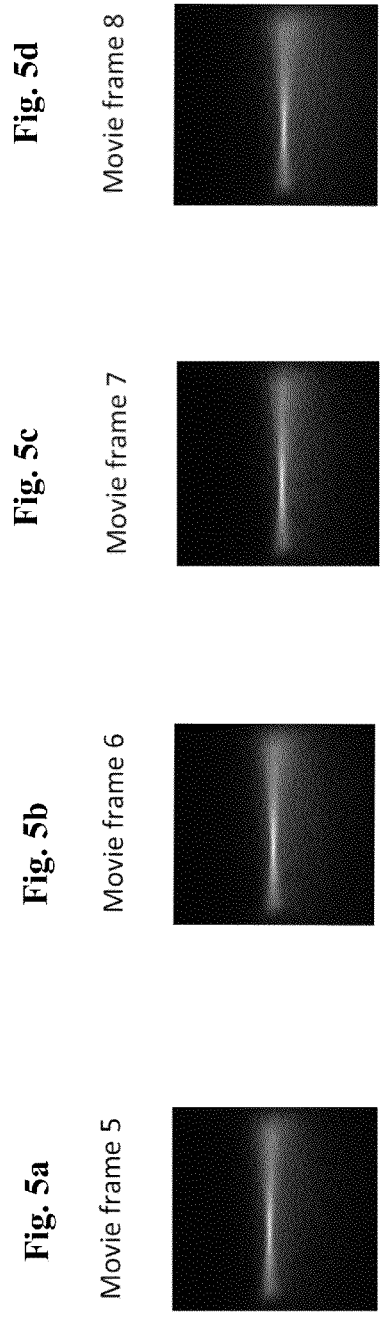
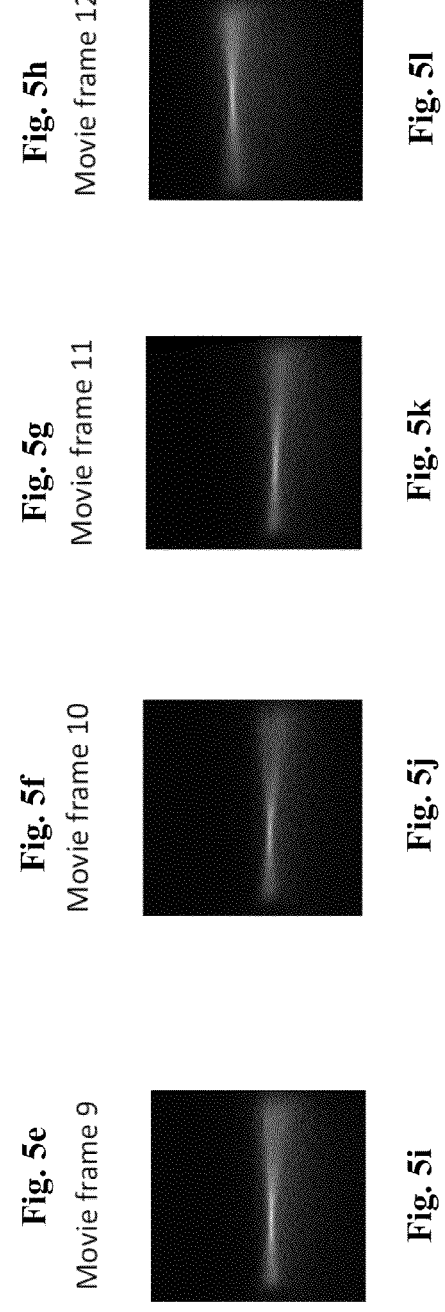

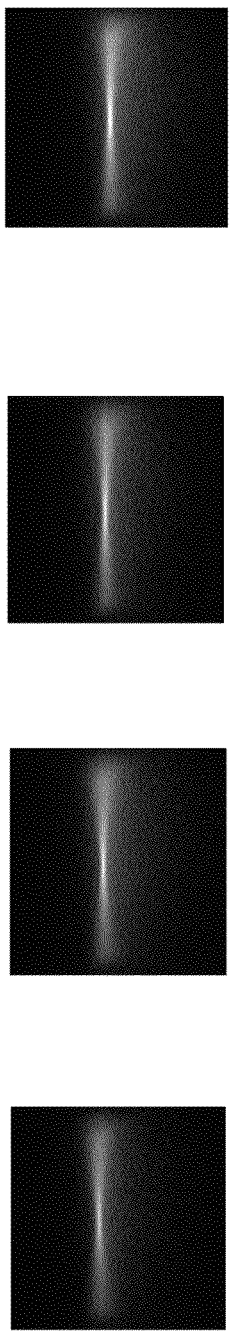
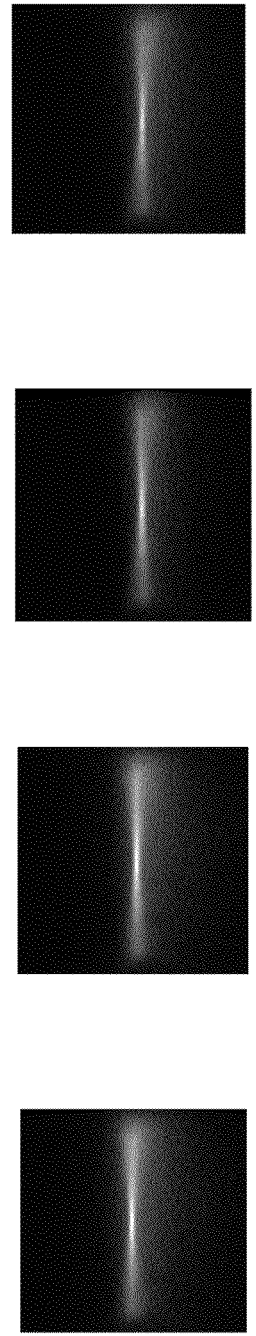
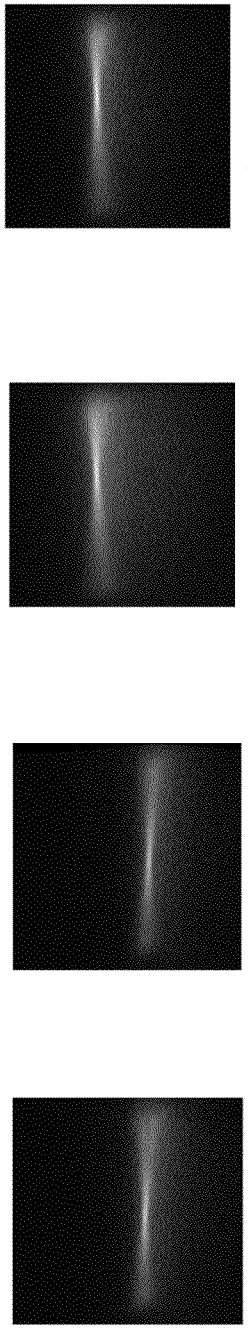
Fig. 5m Movie frame 17
Fig. 5n Movie frame 18
Fig. 5o Movie frame 19
Fig. 5p Movie frame 20
Fig. 5q Movie frame 21
Fig. 5r Movie frame 22
Fig. 5s Movie frame 23
Fig. 5t Movie frame 24
Fig. 5u
Fig. 5v
Fig. 5w
Fig. 5x

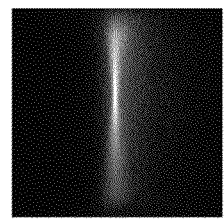
Movie frame 27
Fig. 5aa
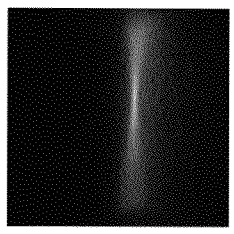
Movie frame 28
Fig. 5bb
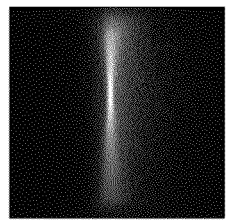
Movie frame 26
Fig. 5z
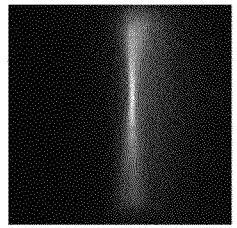
Movie frame 31
Fig. 5ee
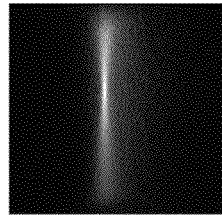
Movie frame 25
Fig. 5y
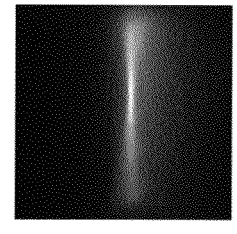
Movie frame 30
Fig. 5dd
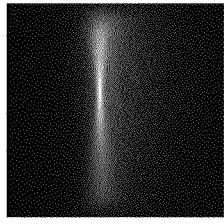
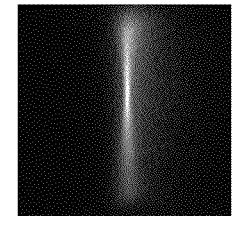
Movie frame 29
Fig. 5cc
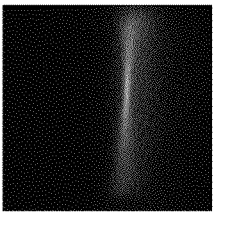
Movie frame 32
Fig. 5ff
Movie frame 33
Fig. 5gg

DEEP TISSUE FOCAL FLUORESCENCE IMAGING WITH DIGITALLY TIME-REVERSED ULTRASOUND-ENCODED LIGHT

CROSS REFERENCE TO RELATED APPLICATIONS

This application claims priority under 35 U.S.C. §119(e) to the following and commonly-assigned U.S. patent application:

U.S. Provisional Patent Application Ser. No. 61/616,347, filed on Mar. 27, 2012, by Ying Min Wang, Benjamin Judkewitz, Charles A. DiMarzio, and Changhuei Yang, entitled "DEEP TISSUE FLUORESCENCE IMAGING USING DIGITALLY TIME-REVERSED ULTRASOUND-ENCODED LIGHT", which application is incorporated by reference herein.

This application is related to the following and commonly-assigned patent applications, which applications are incorporated by reference herein:

U.S. Utility patent application Ser. No. 12/886,320, filed on Sep. 20, 2010, by Zahid Yaqoob, Emily McDowell and Changhuei Yang, entitled "OPTICAL PHASE PROCESSING IN A SCATTERING MEDIUM", which application is a divisional of U.S. Utility patent application Ser. No. 11/868,394, filed on Oct. 5, 2007, by Zahid Yaqoob, Emily McDowell and Changhuei Yang, entitled "TURBIDITY ELIMINATION USING OPTICAL PHASE CONJUGATION AND ITS APPLICATIONS", which application claims priority under 35 U.S.C. §119(e) to commonly-assigned U.S. Provisional Patent Application Ser. No. 60/850,356, filed on Oct. 6, 2006, by Zahid Yaqoob, Emily McDowell and Changhuei Yang, entitled "TURBIDITY ELIMINATION USING OPTICAL PHASE CONJUGATION AND ITS APPLICATIONS";

U.S. patent application Ser. No. 12/943,857, filed on Nov. 10, 2010, by Changhuei Yang and Meng Cui, entitled "TURBIDITY SUPPRESSION BY OPTICAL PHASE CONJUGATION USING A SPATIAL LIGHT MODULATOR", which application claims the benefit under 35 U.S.C. §119(e) of the following and commonly-assigned U.S. provisional patent applications, which are incorporated by reference herein:

a. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES";

b. Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION";

c. Provisional Patent Application Ser. No. 61/376,202, filed on Aug. 23, 2010, by Meng Cui and Changhuei Yang, entitled "OPTICAL PHASE CONJUGATION 4PI MICROSCOPE"; and d. Provisional Application Ser. No. 61/355,328, filed on Jun. 16, 2010 by Meng Cui, Ying Min Wang and Changhuei Yang, entitled "ACOUSTIC ASSISTED PHASE CONJUGATE OPTICAL TOMOGRAPHY";

U.S. Utility application Ser. No. 12/943,841, filed on Nov. 10, 2010, by Meng Cui, Ying Min Wang, Changhuei Yang and Charles DiMarzio, entitled "ACOUSTIC ASSISTED PHASE CONJUGATE OPTICAL TOMOGRAPHY", which application claims priority under 35 U.S.C. §119(e) to and commonly-assigned U.S. Provisional Application Ser. No. 61/355,328, filed on Jun. 16, 2010, by Meng Cui, Ying Min Wang, and Changhuei Yang, entitled "ACOUSTIC ASSISTED PHASE CONJUGATE OPTICAL TOMOGRAPHY"; U.S. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES"; U.S. Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION"; and U.S. Provisional Patent Application Ser. No. 61/376,202, filed on Aug. 23, 2010, by Meng Cui and Changhuei Yang, entitled "OPTICAL PHASE CONJUGATION 4PI MICROSCOPE"; and U.S. Utility application Ser. No. 13/157,194, filed on Jun. 9, 2011, by Meng Cui, Ying Min Wang, and Changhuei Yang, entitled "ITERATIVE TIME-REVERSAL ENHANCED TRANSMISSION SOLVING APPROACH", which application claims the benefit under 35 U.S.C. §119(e) of Provisional Application Ser. No. 61/355,326, filed on Jun. 16, 2010, by Meng Cui, Ying Min Wang, and Changhuei Yang, entitled "ITERATIVE TIME-REVERSAL ENHANCED TRANSMISSION SOLVING APPROACH".

STATEMENT REGARDING FEDERALLY SPONSORED RESEARCH AND DEVELOPMENT

This invention was made with Government support under W31P4Q-11-1-0008 awarded by DARPA and under OD007307 and EB012255 awarded by the National Institutes of Health. The Government has certain rights in this invention.

BACKGROUND OF THE INVENTION

1. Field of the Invention

This invention relates to a method and apparatus for imaging and irradiating scattering media.

2. Description of the Related Art (Note: This application references a number of different publications as indicated throughout the specification by one or more reference numbers in superscript [x]. A list of these different publications ordered according to these reference numbers can be found below in the section entitled "References." Each of these publications is incorporated by reference herein.)

Realizing high-resolution fluorescence imaging within scattering biological tissues is a central goal in biomedical imaging. Considerable efforts have been made to extend the imaging depth of optical methods[1-7], but focal excitation of fluorescence has so far been fundamentally limited to a depth of one transport mean free path, or approximately one millimeter in most biological samples. This is because conventional focusing approaches treat scattered light as noise and select for the ballistic light component, which exponentially decreases with depth. However, scattered light contains important information about the sample, which can in fact be utilized. When light passes through scattering samples, its wavefront is seemingly randomized, but the randomization occurs in a deterministic and time-symmetric way. These properties of elastic light scattering have recently been used to focus light through turbid samples by iterative wavefront optimization[8-15] and by time-reversal using optical phase conjugation[10,16-18]. These methods are, in many ways, analogous to adaptive optics methods used in astronomy to cancel out the effect of atmospheric scattering[19,20]. However, in contrast to astronomy where it is sufficient to image through a turbid medium (the atmosphere), the goal of biomedical imaging is to image inside.

To achieve focusing inside tissues, Xu et. al.[21] proposed a scheme termed time-reversal of ultrasound encoded light (TRUE), which combines optical phase conjugation[22] with ultrasound encoding[23]. They used focused ultrasound, which is much less scattered than light in biological tissues, to create a virtual source of light frequency-shifted by the acousto-optic effect. Scattered light emanating from this source was then time-reversed by a photorefractive crystal acting as a phase conjugate mirror. Xu et. al.[21] inferred the formation of a time-reversed optical focus from a line-scan across milli-meter-scale absorbers embedded in tissue-mimicking phantoms.

While promising improved absorption contrast[21,24,25], the use of this technique for high-resolution fluorescence imaging in biological tissues remains fundamentally challenging. Because of the low ultrasound modulation efficiency[26], the phase conjugate mirror has to provide orders of magnitude higher than unity gain to excite detectable fluorescence. This requirement cannot be met by traditional phase conjugate mirrors based on photorefractive crystals whose gain is typically much less than one[27,28].

Moreover, the significant challenge of undesired background illumination due to partial phase conjugation needs to be addressed. With complete time-reversal, the TRUE focusing technique can be conceptually represented as photons retracing their paths back to the location of the virtual source. However, this view disregards the wave-nature of light: complete time reversal requires full control over phase, amplitude and polarization of the entire scattered field over the full solid angle—which is fundamentally unfeasible (see Section I.1). As a result, even with perfectly aligned optics and noise-free recording of the scattered wavefront, the time-reversed focus is necessarily accompanied by a background[29-31] which would obscure the fluorescence signal originating at the desired optical focus.

One or more embodiments of the present invention present a new strategy to overcome these challenges by combining digital phase conjugation[32] with dynamic wavefront manipulation. The formation of an optical focus can be directly visualized, exciting fluorescence between layers of highly scattering tissue. This provides confirmation of the presence of the accompanying background, predicted by theory, that can be dynamically reproduced and subtracted. This digital background cancellation procedure, along with the high phase conjugate gain and resolution of one or more embodiments of the technique, enable the first demonstration of focused fluorescence imaging 2.5 millimeters deep inside biological tissue.

SUMMARY OF THE INVENTION

Fluorescence imaging is one of the most important research tools in biomedical sciences. However, scattering of light severely impedes imaging of thick biological samples beyond the ballistic regime.

One or more embodiments of the invention directly show focusing and high-resolution fluorescence imaging deep inside biological tissues, by digitally time-reversing ultrasound-tagged light with high optical gain (~5·10$^5$). We confirm the presence of a time-reversed optical focus along with a diffuse background—a corollary of partial phase conjugation—and develop an approach for dynamic background cancellation.

To illustrate the potential of our method, one or more embodiments image complex fluorescent objects and tumor microtissues at an unprecedented depth of 2.5 mm in biological tissues, at a lateral resolution of 36 µm by 52 µm, and at an axial resolution of 657 µm.

The results set the stage for a range of deep tissue imaging applications in biomedical research and medical diagnostics.

For example, one or more embodiments of the present invention include a method for irradiating a scattering medium, comprising:

(a) encoding light, in one or more regions of a scattering medium, with a signal (e.g., ultrasound);

(b) collecting a portion of the encoded light, comprising one or more encoded fields, in a digital optical phase conjugation (DOPC) device comprising a spatial light modulator connected to a camera;

(c) producing, in the DOPC device, one or more time reversed fields that are phase conjugates of the encoded fields of the portion of the encoded light;

(d) irradiating the scattering medium with the time reversed fields, wherein the time reversed fields include a desired component that converges back to the one or more regions, and a background component due to incomplete time reversal resulting from only the portion of the encoded light being collected;

(e) detecting, on a detector, output radiation based on an interaction between the time reversed fields and the scattering medium (e.g., fluorescence), to produce a first detected signal;

(f) irradiating the scattering medium with one or more background fields that at least approximate the background component;

(g) detecting, on the detector, output radiation based on an interaction between the background fields and the scattering medium (e.g., fluorescence), to produce a second detected signal; and (d) subtracting, in a computer, the second detected signal from the first detected signal, to obtain an output that at least approximates an interaction between a complete time reversed field, of all of the encoded light's fields, and the scattering medium. The output can be used to image the scattering medium.

The method can further comprise transmitting one or more of the signals from a source of signals and to one or more regions of a scattering medium; transmitting input light from a laser and through the one or more regions of the scattering medium concurrently with the signals, wherein the signals at least partially modulate the input light into modulated light to form the encoded light, as the input light passes through the one or more regions of the scattering medium concurrently with the signals; collecting, in the DOPC device, the portion of the modulated light transmitted out of scattering medium, as collected modulated light; computing one or more digital phase conjugate fields that are phase conjugates of the collected modulated light's fields; irradiating the one or more regions with the time reversed fields comprising the digital phase conjugate fields; and modifying the digital phase conjugate fields to produce the background fields.

The method can further comprise measuring a phase map of the collected modulated light, wherein the computing comprises digitally phase conjugating the phase map to produce a phase conjugate map; and the modifying comprises digital manipulation of the phase conjugate map in a computer.

The method can further comprise splitting light from the laser into the input light and reference light both having a frequency of the light; modulating, using a modulator, the reference light with a signal frequency, wherein the signals also have the signal frequency and modulate the input light with the signal frequency to form the modulated light; combining the reference light and a portion of the modulated light that has exited the scattering medium, such that the reference light and the collected modulated light interfere and form an interference pattern on the camera; measuring the phase map of the collected modulated light using the interference pattern and a computer, displaying, on the SLM's display placed at an image plane of the camera, the phase conjugate map; irradiating the scattering medium with time reversed light comprising the time reversed fields, by guiding the reference light, wherein the reference light reflects off the SLM display displaying the phase conjugate map to form the time reversed light; modifying the phase conjugate map into a digitally manipulated phase conjugate map by the digital manipulation; displaying, on the SLM's display placed at an image plane of the camera, the digitally manipulated phase conjugate map; irradiating the scattering medium with background light comprising the background fields by guiding the reference light, wherein the reference light reflects off the SLM display displaying the digitally manipulated phase conjugate map to form the background light; and wherein the scattering medium is supported by a holder.

The digital manipulation can comprise digitally shifting the phase conjugate map by a plurality of pixels of the SLM.

The digital manipulation can comprise dividing the phase conjugate map into sub-regions and phase-shifting every other sub-region by a plurality of degrees.

The digital manipulation can comprise compensating for curvature of the SLM; and randomly alternating between at least two trigger delays between the light, comprising pulsed light, and the signals, comprising pulsed ultrasound waves, to counter a phase drift between a non-modulated background, comprising the input light passing through the regions and that is not modulated, and the reference light, wherein the phase drift leads to an added artificial signal on the phase map.

The SLM and the camera can be connected such that one SLM pixel is imaged onto one camera pixel.

The signals can comprise ultrasound waves generated by an ultrasound transducer and focused such that the one or more regions comprise one or more ultrasound foci of the ultrasound waves.

One or more embodiments of the invention further disclose an apparatus for illuminating, imaging, or irradiating a scattering medium, and method for fabricating the same.

For example, the apparatus can comprise:
(a) an ultrasound transducer;
(b) a laser;
(c) a holder for supporting a scattering medium, wherein the ultrasound transducer, the laser, and the holder are connected such that: (i) the ultrasound transducer transmits ultrasound waves to one or more foci in one or more regions of the scattering medium; (ii) the laser transmits input light to the foci in the one or more regions of the scattering medium concurrently with the ultrasound waves, and (iii) the ultrasound waves at least partially frequency shift the input light into modulated light, as the input light passes through the foci concurrently with the ultrasound waves;
(d) a Digital Optical Phase Conjugation (DOPC) device, comprising a digital programmable spatial light modulator (SLM) connected to and imaged onto a digital camera, wherein:
(i) the camera is positioned to collect a portion of the modulated light, that has exited the scattering medium, as collected modulated light, and outputs one or more digital signals in response thereto;

(ii) a computer connected to the DOPC calculates one or more phases of the collected modulated light using the digital signals;
(iii) a computer connected to the DOPC device computes phase conjugate phases that are phase conjugates of the phases,
(iv) the DOPC device irradiates the scattering medium with time reversed fields having the phase conjugate phases, wherein the time reversed fields include a desired component that converges back to the foci, and a background component due to incomplete time reversal resulting from only the portion of the modulated light being collected;
(v) a computer connected to the DOPC phase shifts one or more of the phase conjugate phases by one or more amounts to remove the desired component that converges to the foci, to produce the background fields;
(iv) the SLM is programmed and positioned to sequentially modulate light first with the time reversed fields and then with background fields that at least approximate the background component;
(e) a detector connected to the holder, wherein:
the detector detects radiation transmitted from the scattering medium in response to the time reversed fields, to produce a first detected signal, and
the detector detects radiation transmitted from the scattering medium in response to the background fields, to produce a second detected signal, and
(f) a computer connected to the detector, wherein the computer subtracts the second detected signal from the first detected signal, to obtain an output that at least approximates an interaction between a complete time reversed field, of all of the encoded light's fields, and the scattering medium.

In one embodiment, the camera comprises an analog/digital dynamic range of at least 16 bits; the SLM comprises a resolution of at least 1920 by 1080 pixels and an input frame rate of at least 60 Hz; the DOPC device outputs output light comprising the time reversed fields with a power having a gain of at least $10^5$ as compared to a power of the modulated light collected by the DOPC, and a response time of the apparatus is faster than 6.7 seconds or a decorrelation time of the scattering medium, wherein the response time is a time between the ultrasound waves at least partially frequency shifting the input light into modulated light and the detector detecting radiation transmitted from the scattering medium in response to the background fields.

BRIEF DESCRIPTION OF THE DRAWINGS

Referring now to the drawings in which like reference numbers represent corresponding parts throughout:

FIGS. 5*a*-5*gg* illustrate sequential movie frame images showing that as the position of the ultrasound transducer is scanned, the optical focus follows the locations of the ultrasound focus, according to one or more embodiments of the invention.

DETAILED DESCRIPTION OF THE INVENTION

Figure 1A:
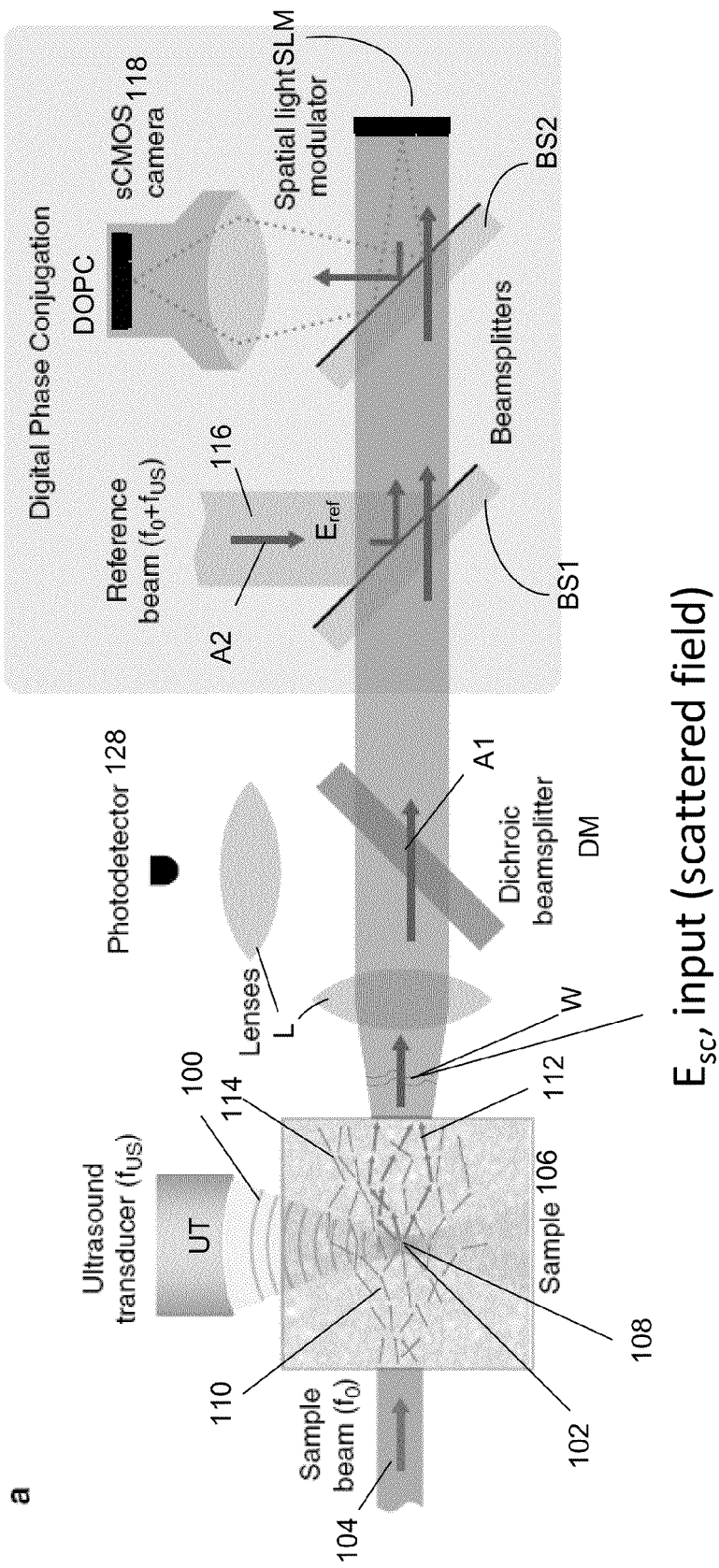
FIG. 1(a) shows a recording step, according to one or more embodiments, wherein a 0.8-mm wide sample beam ($f_0$) scatters as it propagates through the tissue sample, a confined region of the scattered light in the tissue sample is frequency-shifted ($f_0 \pm f_{US}$) by a focused ultrasound pulse, the ultrasound focus thus becomes a virtual source within the tissue, both the frequency-shifted light and the non-shifted light further scatter through the tissue and are collected, this output wavefront interferes with a reference beam ($f_0 + f_{US}$), the resulting interference pattern is imaged onto a scientific CMOS (sCMOS) camera in the digital phase conjugate mirror module, the digital phase conjugate mirror selectively measures the phase map ($\phi(x, y)$) of the frequency-shifted light through digital phase-shifting holography, and the ultrasound is turned off after recording.

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

I. Set Up And Results

1. Apparatus

FIG. 1 diagrammatically illustrates a schematic of an imaging principle, and a setup for fluorescence imaging with time-reversed light, according to one or more embodiments. Since the performance of the approach critically depends on achievable resolution, phase conjugate mirror gain, and fidelity of phase conjugation, these parameters are further discussed below.

FIG. 1 (*a*) illustrates the recording step. An ultrasound pulse 100 having frequency $f_{US}$ from an Ultrasound Transducer UT propagates to an ultrasound focus 102. Light (a 0.8 mm wide sample beam 104 having frequency $f_0$ scatters as it propagates through tissue or a tissue sample 106, resulting in a speckled light field at the ultrasound focus 102. A confined region 108 of the scattered light 110 in the tissue sample 106 is frequency-shifted (to a frequency $f_0 \pm f_{US}$) by a focused ultrasound pulse 100 (the speckles within the ultrasound focus 102 are frequency-shifted via the acousto-optic effect, creating a source of frequency-shifted light). The ultrasound focus 102 thus becomes a virtual source within the tissue. Both the frequency-shifted light 112 and the non-shifted light 114 further scatter through the tissue 106 and are collected.

This output wavefront W interferes with a reference beam 116 (with frequency $f_0+f_{US}$) and the resulting interference pattern is imaged onto a scientific CMOS (sCMOS) camera 118 in the digital phase conjugate mirror or digital phase conjugation module (DOPC). The DOPC selectively measures the phase map ($\Phi(x,y)$) of the frequency-shifted light through digital phase-shifting holography. The ultrasound is turned off after recording. Arrow A1 illustrates the trajectory of the frequency shifted light after it exits the scattering medium 106 with electric field E and propagates to the DOPC. Arrow A2 illustrates the trajectory of the reference beam 116. Also shown are beamsplitters BS1, BS2, and dichroic beamsplitter DM.

Figure 1B:
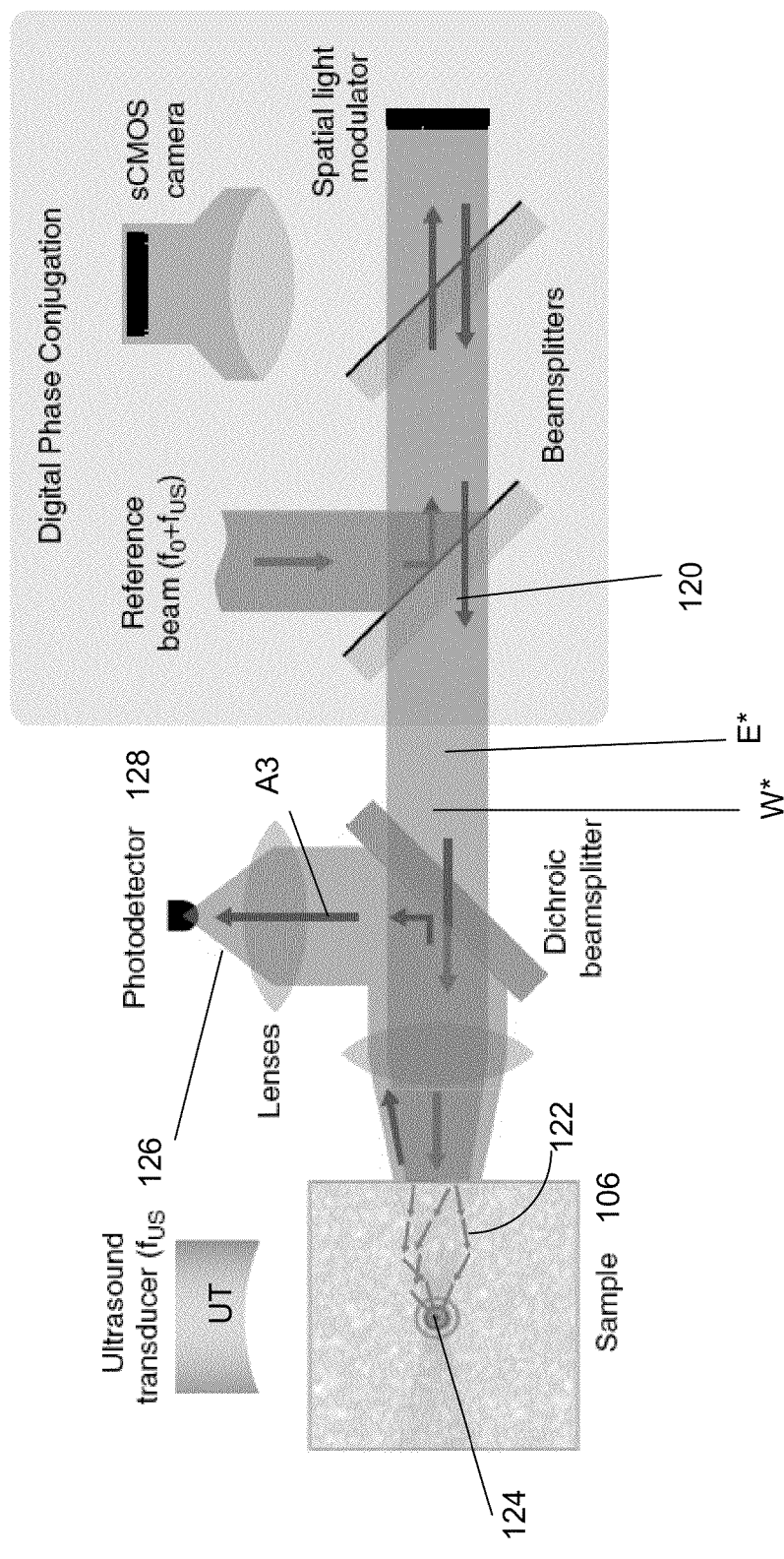
FIG. 1(*b*) illustrates a playback step, according to one or more embodiments, wherein the conjugate of the recorded phase map ($-\Phi(x, y)$) is displayed on a spatial light modulator (SLM) placed at the image plane of the sCMOS camera, the reference beam reflects off the SLM and is transformed into the phase conjugate beam that is propagated back into the tissue, reconstructing an optical focus at the ultrasound modulation location, and any excited fluorescence is collected and measured outside the tissue using a photodetector.
FIG. 1*c* illustrates the experimental setup, according to one or more embodiments, used to obtain all data shown in this disclosure, wherein abbreviations are Pulsed laser source (PLS), Optical Isolator (OI), Half-wave plate (HWP), Polarizing beamsplitter (PBS), Beam dump (BD), Mirror (M), 50/50 cube beamsplitter (BS), Acousto-optic modulator (AOM), Neutral density filterwheel (ND), Path length matching arm (PLM), Single-mode fiber acting as spatial filter (SF), Collimating lens (CL), Sample (S), Ultrasound transducer (UST), 50 mm planoconvex lens (L1), Dichroic beamsplitter (DBS), Interference filter (IF), 25 mm planoconvex lens (L2), Photomultiplier tube (PMT), Polarizer (P), 90/10 plate beamsplitter (PLB1), Digital optical phase conjugation setup (DOPC), 50/50 plate beamsplitter (PLB2), Photography compound lens (PL), sCMOS camera (sCMOS), Spatial light modulator (SLM), 300 mm piano-convex lens (L3), Microscope objective (MO), and Diffuser disk (DD).
FIG. 1*d* illustrates timing of acquisition information, according to one or more embodiments.
FIG. 1*e* illustrates the effects of coherence length (coherence length limits detection of scattered photons), according to one or more embodiments.

FIG. 1(b) illustrates the playback step, wherein the conjugate of the recorded phase map ($-\Phi(x,y)$) is displayed on a spatial light modulator (SLM) placed at the image plane of the sCMOS camera 118. The reference beam 116 reflects off the spatial light modulator SLM and is transformed into the phase conjugate beam having electric field E* and wavefront W* that is propagated 120, 122 back into the tissue, reconstructing an optical focus 124 at the ultrasound modulation location. Any excited fluorescence 126 is collected and measured outside the tissue using a photodetector 128. The fluorescence trajectory is illustrated by arrow A3.

Since the technique selectively records and phase conjugates the frequency-shifted light, the size of the ultrasound-modulated volume determines the resolution of the phase conjugated optical focus. FIG. 1 illustrates the use a high numerical aperture focused ultrasound with a calculated focal width of 34 µm. To further confine the ultrasound-modulated volume along the axis of ultrasound propagation, both the ultrasound source and the laser are operated in pulsed mode[33] such that light only enters the sample when the ultrasound pulse has reached the target modulation volume (calculated resolution along the axis of ultrasound propagation: 54 µm).

Figure 1C:
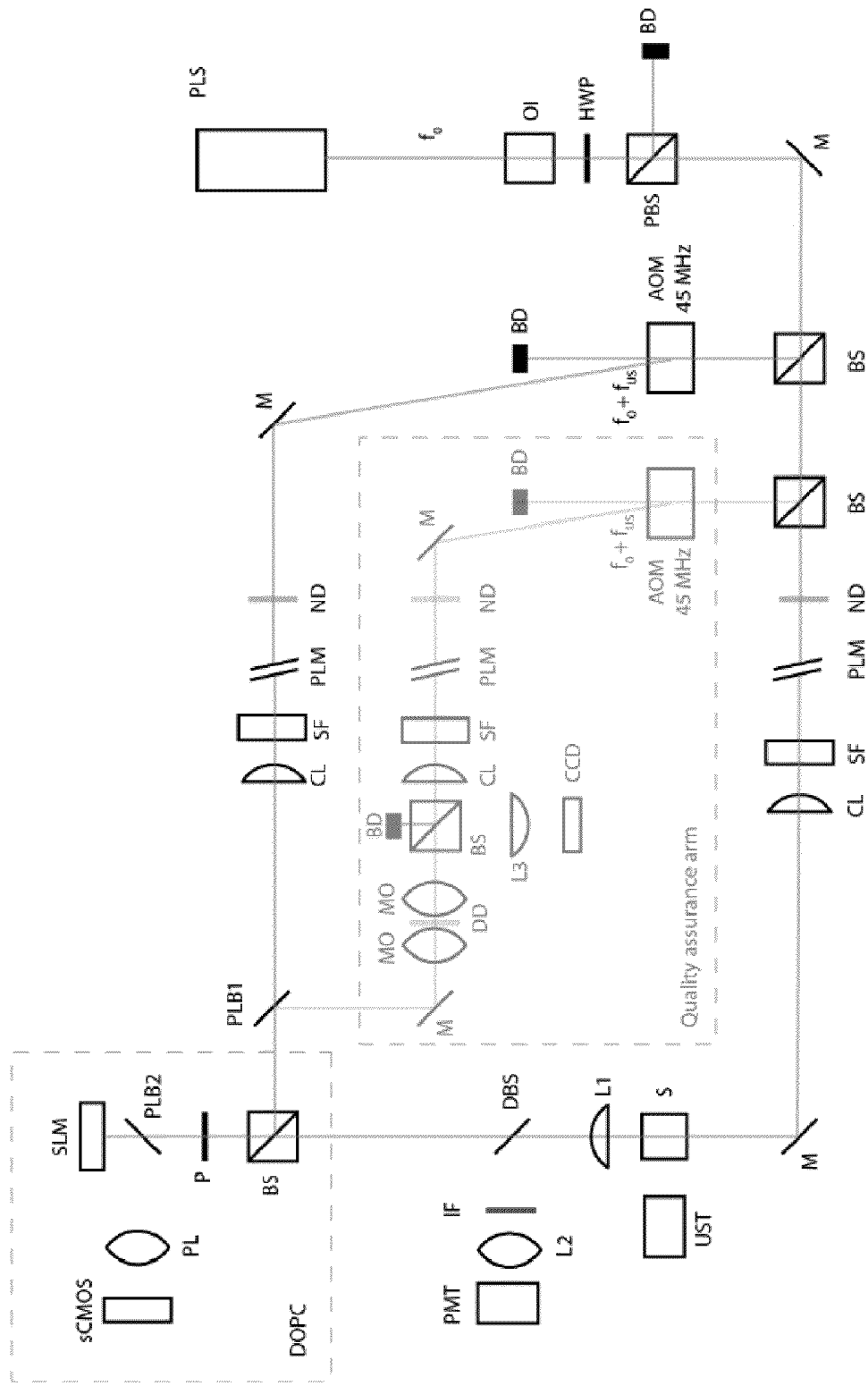
Figure 2:
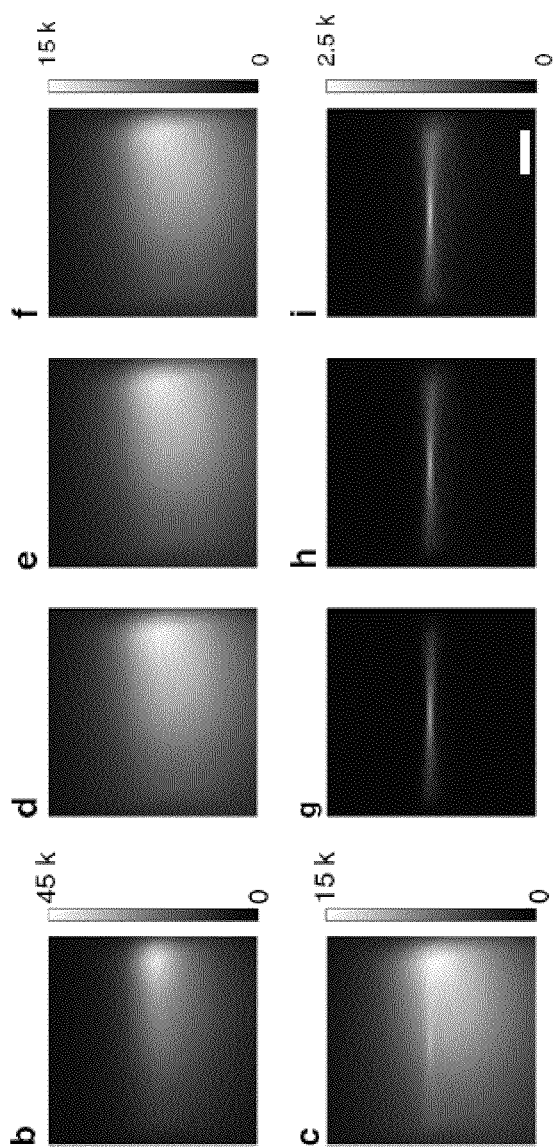
FIG. 2 illustrates demonstration of optical focusing between thick layers of biological tissue, according to one or more embodiments of the invention, wherein (a) is a Schematic of the sample arrangement, consisting of a thin sheet of quantum dots (Qdot) between two 2.5 mm thick sections of ex vivo chicken tissue, (b-d) Fluorescence emission camera images of the area (in the y-z plane) indicated by the dashed square in (a), (b) shows diffuse illumination pattern obtained by focusing into the tissue without wavefront modulation (flat phase display on the SLM), (c) shows the illumination pattern resulting from optical phase conjugation of ultrasound-tagged light, showing a focus on top of a diffuse Background, (d-f) show background images and (g-i) show corresponding background subtracted maps (positive values) obtained by the following techniques: (d, g) mechanically shifting the sample by 5 μm to disrupt phase conjugation; (d, h) digitally shifting the phase map by 50 pixels; and (f, i) modulating the original phase map by subdividing it into 8×16 areas and alternately adding 0 or π phase shift to each area, and wherein the scale bar is 500 μm.
Figure 2:
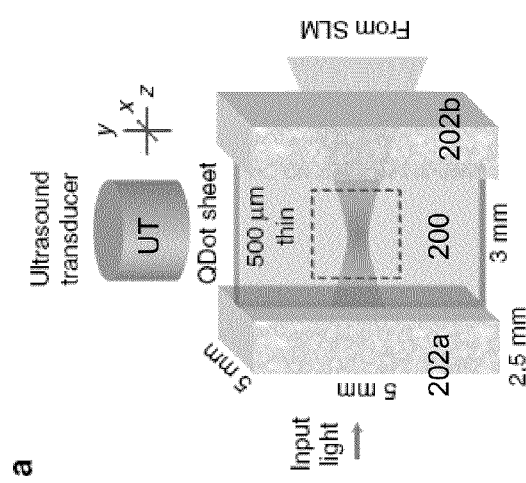
Figure 3:
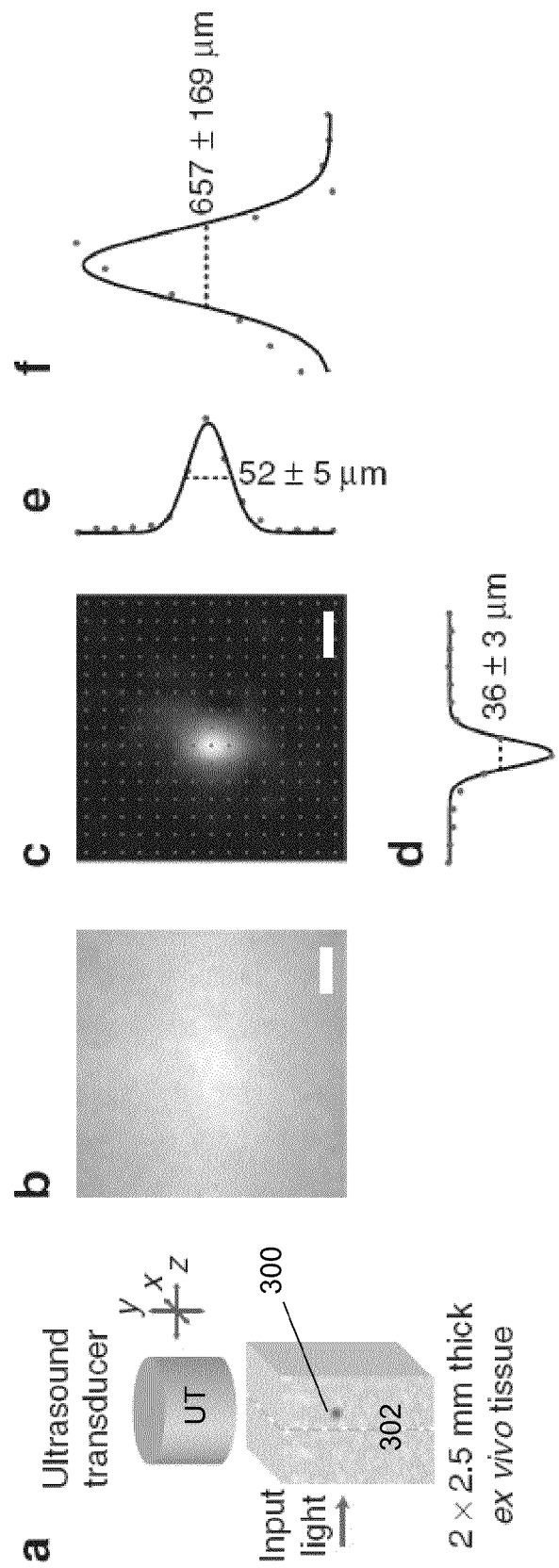
FIG. 3 illustrates determination of point spread function, wherein (a) shows the schematic of the setup used for the point spread function measurement where a fluorescent bead is embedded between two 2.5 mm thick sections of ex vivo tissue, (b) shows epifluorescence image of the sample in the xy plane, showing very strong blurring due to tissue scattering, (c) shows fluorescence image obtained by scanning the position of the ultrasound transducer in x and y, detecting the fluorescence excited by time-reversed light and using adaptive background cancellation as described in the text, (d-f) shows the Profile of the fluorescent bead in x(d), y(e) and z(f) direction and the dots indicate locations of collected data points, pixels between data points are interpolated for display using bicubic interpolation and the scale bar is 50 μm.
Figure 4:
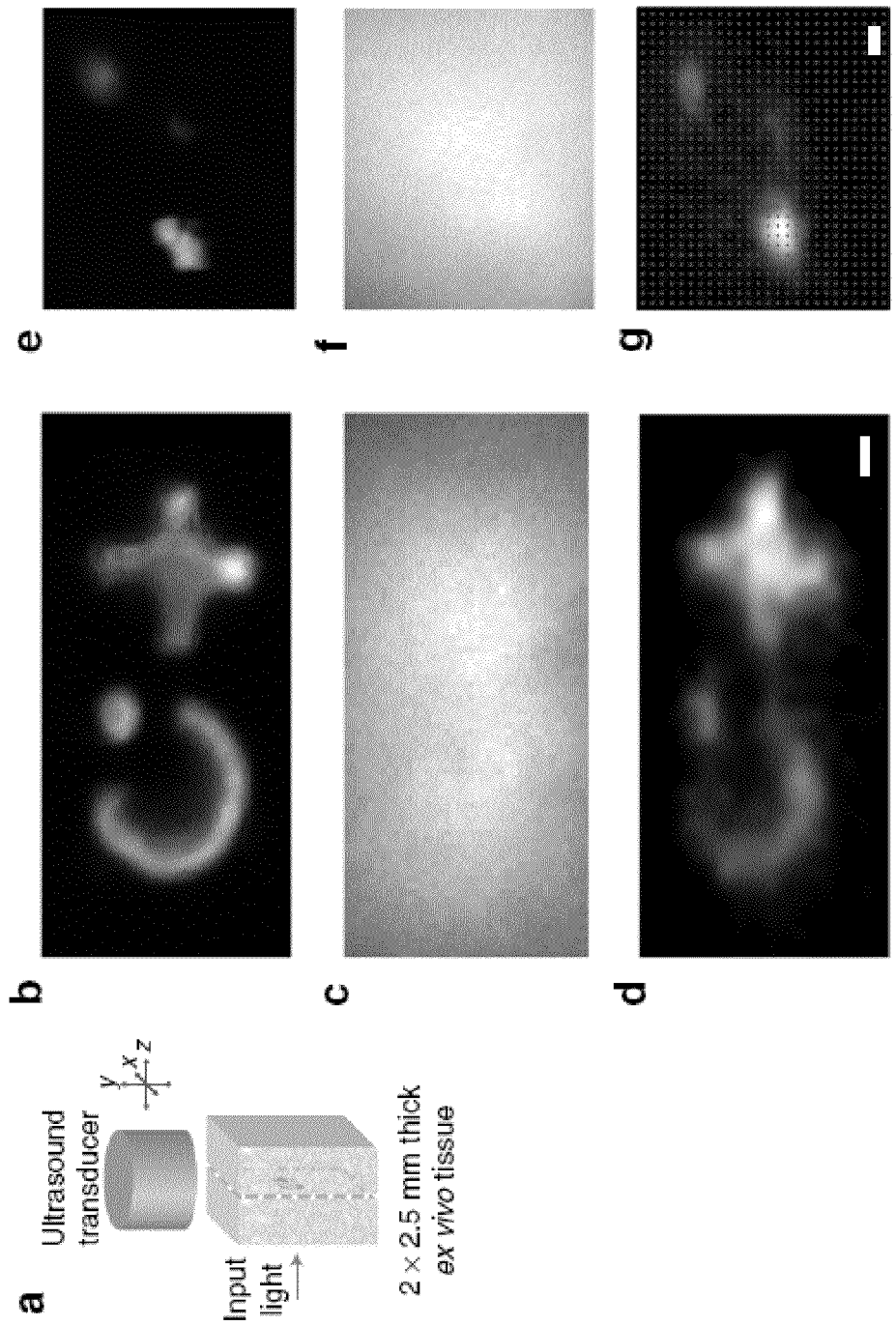
FIG. 4 illustrates fluorescence images of a complex object, according to one or more embodiments of the invention, wherein FIG. 4 (*a*) illustrates diagram of sample arrangement, FIG. 4(*b*) illustrates epi fluorescence image of an abstract "CIT" feature, FIG. 4(*c*) illustrates epifluorescence image obtained when the sample is placed under 2.5 mm of biological tissue and the features are not resolved, FIG. 4(*d*) illustrates a raster scanned image of the embedded "CIT" feature obtained using the imaging system of FIG. 1*a*, FIG. 4(*e*) is Epifluorescence image of tumor microtissues, FIG. 4(*f*) is Epifluorescence image obtained when the sample is placed under 2.5 mm of biological tissue, and FIG. 4(*g*) is Raster-scanned image of the embedded tumors obtained using our imaging system of FIG. 1*c* (dots indicate locations of collected data points and pixels between data points are interpolated for display using bicubic interpolation, scale bars are 50 micrometers).

FIG. 1(c) an experimental setup, according to one or more embodiments, used to record all data shown in FIGS. 2-4. FIG. 1(c) illustrates a 2.7 W, 532 nm Q-switched laser (Navigator, SpectraPhysics, USA) pulsed at 20 kHz with a pulse width of 7 ns and a coherence length of 7 mm was used as a light source at optical frequency $f_0$. After passing an optical isolator and a fixed attenuator, it was split into a reference beam and a sample beam. The sample beam was attenuated by a neutral density filter wheel, spatially filtered by a single mode optical fiber (Nufern 460HP, 20 cm length), collimated to a 0.8 mm waist beam and directed into the sample cuvette. The irradiance at the sample is 10 mW/mm². We note that this is above the ANSI standards for skin irradiance (2 mW/mm²). However, we do not foresee lowering the laser power as being a fundamental limitation.

Inside the sample, a fraction of the light was frequency-shifted to $f_0+f_{US}$ by an ultrasound transducer (element size: 6.35 mm, focal length: 6 mm; V3330, Olympus NDT, USA) operated at $f_{US}$=45 MHz. To achieve maximal resolution along the axis of ultrasound propagation, the transducer was driven with short pulses (pulse length: 1 cycle at 45 MHz, 55 V peak-to-peak) triggered by the laser Q-switch signal at a fixed delay such that the ultrasound pulses coincided with the laser pulses at the ultrasound focus[33] (the trigger delay was jittered by ±5.5 ns to minimize the detection of coherent effects between ultrasound-tagged and untagged light, see Section II.3).

To scan the ultrasound focus, the transducer was mounted on a three axis computer-controlled micromanipulator (Sutter Instruments, USA). After passing through the sample, the scattered beam was recombined with the reference beam (horizontally polarized), which had also been frequency shifted by $f_{US}$ by an acousto-optic modulator (AFM-502-A1, IntraAction, USA). After passing a horizontally aligned polarizer and another beamsplitter, the combined beams reached the surface of a phase only spatial light modulator (SLM; vis-PLUTO, Holoeye, Germany), carefully aligned (1:1 pixel-to-pixel match) to the image plane of a high dynamic range sCMOS camera (pco.edge, PCO AG, Germany). The lens used to image the SLM onto the sCMOS camera was a commercial compound lens (Nikon Micro-Nikkor 105 mm f/2.8).

Compared to the digital optical phase conjugation system first described by Cui and Yang[32], one or more embodiments of our improved digital optical phase conjugation (DOPC) system directly imaged SLM pixels onto CCD pixels and thus enabled reliable alignment and day-to-day quality assurance (see below). Since the image in this embodiment had to be reflected by a beamsplitter, we chose a plate beamsplitter (High-Energy Nd:YAG 50/50, Newport Corporation, CA) whose reflective surface faced both SLM and camera, to avoid image aberrations and ensure precise alignment.

2. Gain

With traditional phase conjugate mirrors, the power in the phase conjugated beam ($P_{OPC}$) is proportional to the power in the signal beam ($P_S$)[28]. This proportionality is referred to as the gain of the phase conjugate mirror:

$$G = \frac{P_{OPC}}{P_S} \qquad \text{Eq. 1}$$

Because of the low ultrasound modulation efficiency and the small area ratio between ultrasound focus and scattered wavefront, the scattered light field reaching the phase conjugate mirror consists mostly of light that is not frequency-shifted ($f_0$) and a minute fraction (in the setup of FIG. 1a, $10^{-5}$-$10^{-4}$ of the total power) of frequency-shifted, ultrasound-tagged light ($f_0 \pm f_{US}$). Therefore, to excite detectable fluorescence at the optical phase conjugate focus, a phase conjugate mirror with a gain orders of magnitude larger than unity is required. This is currently not achievable by traditional phase conjugate mirrors, even with advanced phase conjugation schemes[4-36].

To selectively phase conjugate only the frequency-shifted light with high gain, the setup of FIG. 1a implements an improved digital optical phase conjugation scheme (DOPC) that consists of a high dynamic range sCMOS camera and a high-resolution phase-only spatial light modulator (SLM)[32]. The scattered, ultrasound-tagged light field interferes with an equally frequency-shifted reference beam ($f_0+f_{US}$) and is imaged onto the sCMOS camera. Using digital phase-shifting holography[37], the phase of the frequency-shifted wavefront ($\Phi(x,y)$) with respect to the reference beam is measured. By reflecting off a phase-only spatial light modulator displaying a phase conjugate map ($-\Phi(x,y)$) at the image plane of the camera, the same reference beam is modulated to become a phase-conjugate beam that is sent back into the sample (FIG. 1b). The phase-conjugate beam traverses back through the tissue sample to converge at the location of the ultrasound focus resulting in an optical focus deep inside the tissue sample.

In the DOPC setup of FIG. 1a, the power in the phase conjugate light that leaves the DOPC setup is only dependent on the power in the reference beam that reflects off the SLM displaying the phase conjugate map; thus, the DOPC is fundamentally not limited in terms of gain (Eq. 1). One or more embodiments have adjusted the intensity of the reference beam during playback to achieve a gain of ~5×10⁵, such that the phase conjugate focus contains sufficient energy to excite fluorescence that can be collected and detected outside of the tissue by a photomultiplier tube (PMT).

Theoretically, with complete phase-conjugation, the light field within the ultrasound focus can be reconstructed without error (see Section II.1 below). However, the assumption of complete phase-conjugation breaks down in practice—real phase-conjugate mirrors, whether based on photorefractive crystals or spatial light modulators, have finite etendue and can only intercept a fraction of the output wavefront. As a result, a background always exists in the case of partial phase conjugation[29-31]. In a random scattering medium, the ratio of the peak intensity of the phase conjugate focus to the average intensity of the accompanying background, the peak-to-background ratio (PBR), can be analytically derived. Following the framework of Vellekoop et. al.[38], we find that the peak-to-background ratio is determined by the number of optical modes intercepted and time-reversed by the phase conjugate mirror, N, and the number of input modes in the ultrasound focus, M (see Section II.2 below). When both phase and amplitude of the scattered field are time-reversed, a case similar to the use of traditional phase conjugate mirrors, the peak-to-background ratio is:

$$PBR_{phase\ \&\ amplitude} = \frac{N+1}{M} \qquad \text{Eq. 2}$$

When only the phase of the scattered field is time-reversed, a case similar to our technique employing the DOPC, the peak-to-background ratio for large N is:

$$PBR_{phase\ only} = \frac{\frac{\pi}{4}(N-1)+1}{M} \approx \frac{\pi}{4} \cdot PBR_{phase\ \&\ amplitude} \qquad \text{Eq. 3}$$

Since N is finite in a real phase conjugation setup, a phase conjugate background is inevitable. In the experimental setup of FIG. 1a, N is limited by the number of optical modes imaged onto the spatial light modulator and the fact that only the horizontally polarized component is measured and time-reversed. The diffuse background that inevitably results can excite fluorophores outside of the focus, contributing to noise in the detected fluorescence signal. Because of its spatial extent, the total background excitation can drown the desired focal fluorescence signal detected by a single channel PMT outside the sample. Our experiments show that this background, though indeed significant, can be dynamically subtracted by digital manipulation of the measured phase conjugate map, allowing us to realize high-resolution focal fluorescence imaging in biological tissues.

3. Direct Visualization of Optical Focus

FIG. 2a illustrates a setup to directly visualize and characterize the focus formed by time-reversed light, comprising an optically transparent hydrogel slab 200 containing a thin quantum dot layer placed between two pieces of ex vivo chicken breast tissue 202a-b, each 2.5 mm thick (FIG. 2a). When light was focused into the tissue without any wavefront manipulation (flat phase display on the spatial light modulator), the light was highly scattered and failed to form a focus (FIG. 2b). In contrast, FIG. 2c shows the fluorescence excited by phase conjugation of ultrasound frequency-shifted light. A cone of light converging into the location of the ultrasound focus was clearly visible, albeit on a significant background. Taking into account the thickness of the quantum dot sheet (500 μm) and the expected size of the ultrasound focus (34 μm, see Section I.5), the peak to background ratio was determined as ~5.5.

FIG. 2(c) illustrates the illumination pattern resulting from optical phase conjugation of US-tagged light, showing a focus on top of a diffuse background (FIG. 2d-f) background images and background subtracted maps (positive values) obtained by the following techniques: (i) mechanically shifting the sample by 5 μm to disrupt phase conjugation, as shown in FIG. 2g (ii) digitally shifting the phase map by 50 pixels, as shown in FIG. 2h, and (iii) modulating the original phase map by subdividing it into 8×16 areas and alternately adding 0 or π phase shift to each area, as shown in FIG. 2i (see also Section I.11).

4. Background Subtraction

As discussed in the above, the diffuse background seen in FIG. 2c is to be expected because of the lack of complete control of the entire light field in a phase conjugation experiment. We further observed that the diffuse background was concentrated around the focus, an effect that was also reported by Vellekoop and colleagues when focusing light through a layer of highly scattering zinc oxide particles[29]. As the number of speckles in the focus increases (see Section I.1), the presence of this background drastically reduces the contrast at the focus and poses a critical challenge to optical focusing using time-reversal. With the DOPC system, however, the ability to digitally manipulate the phase conjugate field allows for the possibility of playing back a light field that closely mimics the background, thus enabling background subtraction.

Accurate background subtraction requires better understanding of the cause of its spatial localization. One possible explanation of this effect is that it is caused by correlations in the scattering transmission matrix[29]. Thus, like the fidelity of the optical phase conjugate focus, the presence of a concentrated background would depend on the precise alignment of the sample with the phase conjugated beam. Alternatively, the observed background could be caused by the macroscopic concentration of diffuse light around the target area—an effect that would be expected to be more prominent in highly forward-scattering samples such as biological tissues, and that would be invariant to microscopic misalignments of the sample.

FIG. 2d illustrates a method to isolate the dominant effect contributing to the background in our forward-scattering sample, wherein the sample is displaced by 5 μm and displayed the conjugate of the phase map recorded before the displacement. As can be seen in FIG. 2d, this shift entirely disrupted the focused beam, while the diffuse background was unaffected. After subtraction of this background from the raw image, a focus was revealed at much higher contrast (FIG. 2g). However, mechanical displacement is an impractical method for background subtraction for most applications. Instead, we can digitally alter the recorded phase maps to mimic the diffuse background illumination. We achieved this by two methods: digitally shifting the phase map by 50 pixels (FIG. 2e, h) or dividing phase maps into large sub-regions and phase-shifting every other sub-region by x (FIG. 2f, i—see Section I.11)—a strategy related to differential background rejection techniques previously used in two-photon microscopy[40,41]. Since digital shifting may introduce undesirable asymmetry to the phase map, the latter method for background subtraction was chosen for all subsequent experiments. We note that a suitable background image could not be obtained by simply displaying a flat phase map on the SLM (as shown in FIG. 2b). Such approach would fail to adapt to different locations of the ultrasound focus and would be unable to compensate for geometrical aberrations in the tissue.

Performing time-reversal and subtracting the background in this manner for each location of the focus, we scanned the position of the ultrasound transducer and confirmed that the optical focus followed the locations of the ultrasound focus, as shown in FIGS. 5a-5ff, which are successive frames of a movie.

5. Determining the Point-Spread-Function

FIG. 3 illustrates determination of point-spread-function.

FIG. 3a illustrates a setup to measure the point-spread-function and to quantify the resolution of our imaging system, wherein a fluorescent quantum dot 300 filled polyacrylamide bead (<20 m in diameter) is placed between two pieces of ex vivo chicken breast tissue 302. FIG. 3b shows an epifluorescence image of this sample. Due to the forward scattering nature of the biological sample (g=0.965,[42]), the approximate location of the bead can be inferred. However, tissue scattering results in very strong blurring that would prohibit imaging at high resolution.

In contrast, FIG. 3c shows a well-resolved image of the bead collected using time-reversed light. To obtain the image, the ultrasound focus was scanned in the XY plane and an optical focus obtained by phase conjugation was formed at each scan position indicated by the blue dots. Background subtraction by dynamic digital phase map manipulation was performed at every step. Since the bead is smaller than the ultrasound focus, the imaged size of the bead effectively estimates the three-dimensional resolution of the imaging system. The profiles in each dimension (FIG. 3d,e,f corresponding to the X, Y and Z dimensions respectively) were fit by Gaussian point spread functions with widths of 36±3 µm and 56±5 µm (full width at half maximum) respectively in the plane perpendicular to the axis of light propagation, and 657±169 m along the axis of light propagation (values±95% confidence of fit).

6. Fluorescence Image of Complex Objects Embedded in Tissue

The deep tissue imaging capability of the system of FIG. 1c can be demonstrated by raster scanning a known complex feature.

FIG. 4a illustrates patterned quantum dot features of an abstract "CIT" design in a 500 µm thin patch of polyacrylamide gel (a hydrogel that is commonly used for ultrasound phantoms[43]), embedded between two pieces of chicken tissue, each 2.5 mm thick. FIG. 4b shows an epifluorescence image of the features before embedding. Due to tissue scattering, the embedded features cannot be resolved with epifluorescence imaging (FIG. 4c). In comparison, the "CIT" features are clearly resolved using the method of FIG. 1, as shown in FIG. 4(d).

7. Fluorescence Image of Embedded Tumor Microtissues

One or more embodiments of the invention also obtained images of tumor microtissues embedded in tissues. The microtissues are arranged in a 500 µm thin patch of polyacrylamide gel, embedded between two pieces of chicken tissue, each 2.5 mm thick. FIG. 4e shows an epifluorescence image of the tumors. The tumors embedded between ex vivo tissue are not resolved with epifluorescence imaging (FIG. 4f). In contrast, the tumors imaged with the method of FIG. 1 are well resolved and the differential fluorescence intensities of the tumors are also reflected in the image (FIG. 4g).

8. Sample Preparation for the Samples Measured in FIGS. 2-4

Frozen ex vivo chicken breast tissue was cut into 2.5 mm thick slices and embedded in 10% polyacrylamide gel inside an open-top quartz glass sample cuvette with four polished sides (Starna Cells, CA). The tissue slices had a measured scattering coefficient of $\mu_s$=30 mm$^{-1}$ (see also[31]). Using the previously published anisotropy[42] of g=0.965, we calculated the reduced scattering coefficient as $\mu_s'=\mu_s \cdot (1-g)$=30/mm·(1-0.965)=1.05/mm. This is in agreement with the widely referenced approximate value of ~1/mm (see e.g.[5,21]).

The fluorescent beads measured in FIG. 3 were fabricated as follows. Polyacrylamide gel (PAA) was polymerized using 4 ml phosphate buffered saline, 1.5 ml Acrylamide, 0.4 ml Bis-acrylamide, 62.5 µl Ammonium persulfate and 25 µl Tetramethylethylenediamine. Polyacrylamide beads containing quantum dots (Qtracker 655 Non-targeted Quantum Dots, Invitrogen), were made using a reverse micelle protocol modified from Beningo and Wang[52] with a starting concentration of 200 nM quantum dots in the aqueous phase. The beads obtained varied in size and were strained through a 40 µm cell strainer (Biologix, USA). The actual sizes of the beads used in all experiments were determined by observation under a fluorescence microscope.

The "CIT" feature of FIG. 4 was made by polymerizing clear PAA (500 µm thick) on a SU-8 mold (designed in-house, manufactured by the Stanford Microfluidics Foundry). The patterned depression in the clear PAA gel was then filled with PAA containing quantum dots (Qtracker 705 Non-targeted Quantum Dots, Invitrogen) with a starting concentration of 1 µM in the aqueous phase.

Cancer microtissues, obtained by the hanging-drop technique using HepG2 cells[53], were custom ordered from InSphero AG (Switzerland). The spheroids were fixed with 2% PFA (Sigma-Aldrich, USA), washed with 50 mM borate buffer saline (Thermo Scientific, USA), permeabilized with 0.1% Triton-X 100 (Sigma-Aldrich, USA), and stained with DY-521XL long stokes shift NHS-ester dye (Dyomics, Germany) that binds to the proteins in the cancer microtissues. The concentration of the staining solution was 14 nM. Based on calibration with known fluorophore concentrations, we estimated the resulting stain concentration in the tumor to be ~5 µM. The tumor microtissues were arranged and embedded in a 500 µm thin PAA gel patch.

9. Measurement of Sample Scattering Coefficient

The scattering coefficient of the chicken tissue was measured interferometrically with a Mach Zehnder interferometer. Since only ballistic light will significantly interfere with the reference beam, the reduction in amplitude of the fringes with and without a sample in the sample beam path can be used to find the scattering coefficient.

10. SLM Curvature Compensation

The reliability of digital optical phase conjugation critically depends not only on the precise alignment of SLM and camera, but also on the SLM curvature and reference beam aberrations. Both of these effects can be compensated for digitally by finding a compensation phase map for the SLM that, when displayed, time-reverses the reference beam. Because a time-reversed beam would trace its path back through the spatial filter (the SM fiber), the compensation map was optimized by maximizing the power of the light that returned back through the single mode fiber (measured by a photodiode).

11. Phase Recording

In one or more embodiments, at each scan position, phase recording was achieved in a phase-shifting digital holography setup[37]: the ultrasound pulse was cycled through four phases (0, $\pi/2$, $\pi$, $\pi/2 \cdot \pi$). 10-30 frames were recorded (at 30 frames/second) for each phase and averaged, resulting in four intensity maps ($I_0$, $I_{\pi/2}$, $I_\pi$ and $I_{3/2 \cdot \pi}$), which were used to reconstruct the complex field according to $E=(I_{\pi/2}-I_{3/2 \cdot \pi})+i \cdot (I_0-I_\pi)$.

The phase map was calculated as $\Phi=\tan_{-1}(\text{Re}(E)/\text{Im}(E))$ (or $\Phi=\text{Arg}(E)$). To minimize artifacts introduced by slow phase fluctuations of the reference beam, the acquisition of the intensity maps was interleaved by cycling through all four phases for each block of four sequential frames acquired by the sCMOS camera (exposure time: 28 ms, frame rate: 30 Hz). To achieve sufficiently fast cycling and between-frame switching, an arbitrary function generator (AFG 3252, Tektronix, USA) generated two output signals (one 45 MHz sinusoidal cycle with phase-shift of 0 or $\pi/2$), which were each inverted by a RF 180° power splitter (Mini-circuits, USA) to obtain the four phase-shifted signals. A microcontroller board (Arduino, Italy; obtained from SparkFun Electronics, USA) connected to an RF switch (Mini-circuits, USA) was programmed to select the appropriate phase for each frame acquired by the sCMOS camera. Throughout the phase recording, the SLM displayed a flat (all 0) phase map. An acquisition cycle took 6.7 s/pixel. For complete timing information, see FIG. 1(d).

Figure 1D:
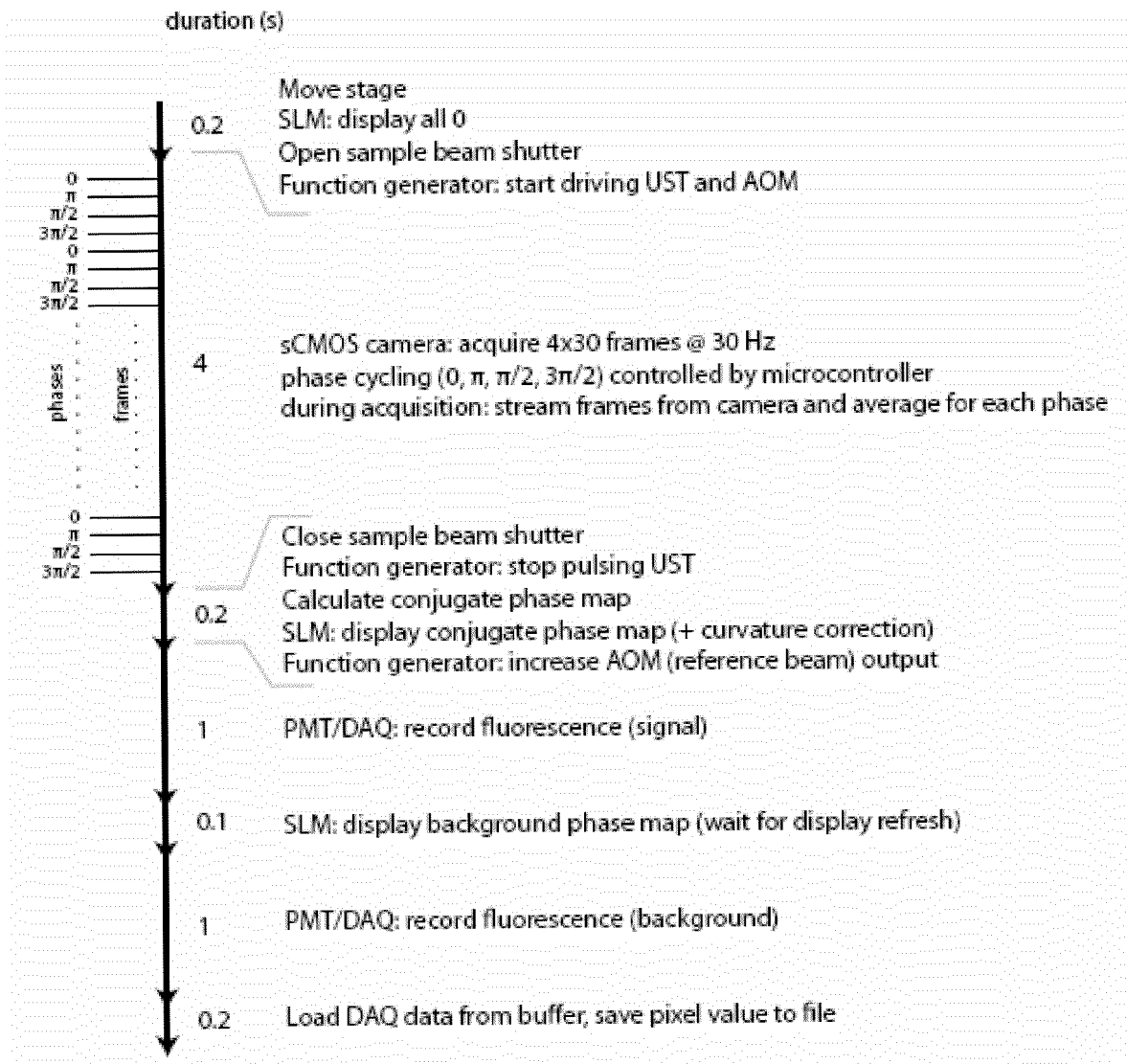

In FIG. 1(d) abbreviations are: Spatial light modulator (SLM), Ultrasound Transducer in sample beam path (UST), Acousto-optic modulator in reference beam path (AOM), Photomultiplier (PMT), Data acquisition device (DAQ), (2) for sequential camera exposures (from frame to frame), the phase is cycled between 0, $\pi$, $\pi/2$ and $3\pi/2$. Frames corresponding to each respective phase are averaged. The averaged data for each phase shift is used for the calculation of the phase maps. The total duration for acquisition of each data point is 6.7 seconds.

Figure 1E:
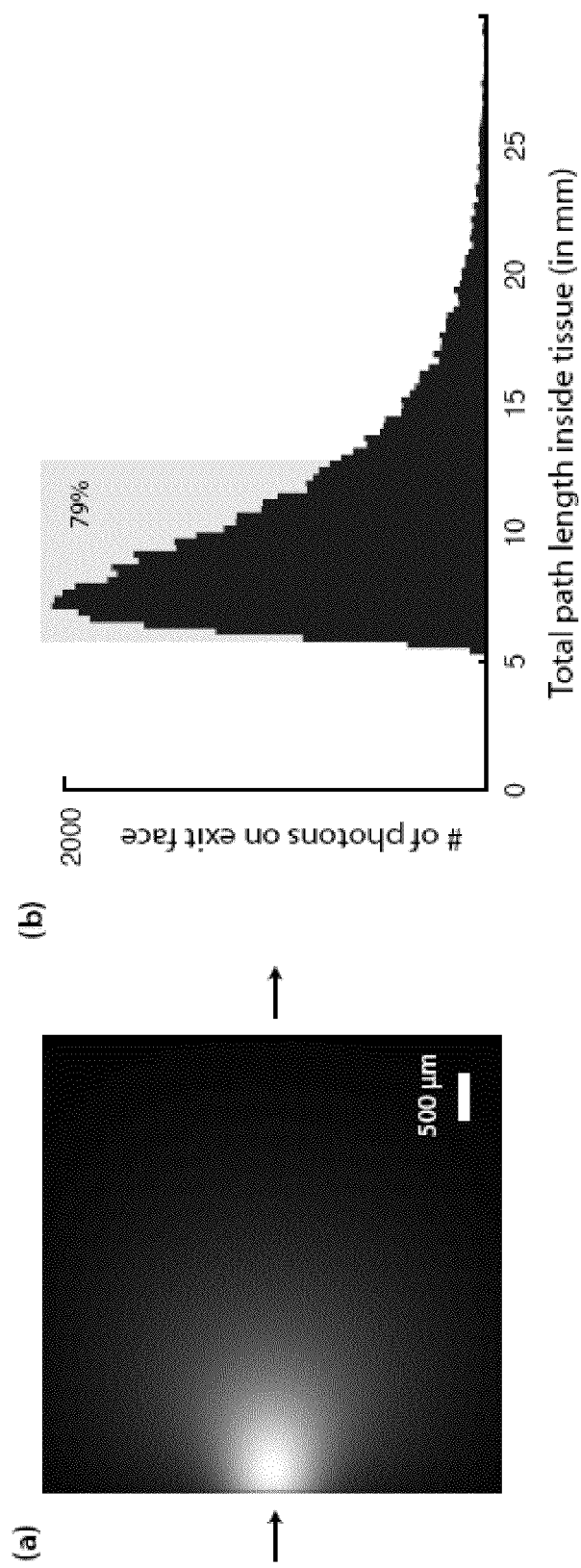

For an analysis the coherence length limits detection of scattered photons, see FIG. 1(e). The Effects of coherence length: Only those scattered photons whose path lengths have not spread beyond the laser coherence length (in the case of FIG. 1c: 7 mm) will be detected by the phase-shifting holography scheme. To confirm that most of the scattered photons fall within this window, we ran a single layer Monte Carlo simulation of photon transport [53], where a 0.8 mm wide (FWHM) collimated gaussian beam was incident on a (5 mm)3 cube of tissue, mimicking the two 2.5 mm thick slabs in our experiments ($\mu_s$=30/mm, g=0.965). We launched 106 photons in this simulation. (a) shows a 2D projection of the normalized photon flux. The path length distribution of the photons leaving the exit face is plotted in (b). We find that 79% of the scattered photons fall within a 7 mm window, thus confirming that the majority of the photons will be detected and time-reversed. Scale bar: 500 μm.

A typical ultrasound tagged phase map recorded on the CCD contained N=$8\times10^4$ modes (area of the sensor divided by speckle autocorrelation area). Together with an estimated M of the ultrasound focus of $1-2\times10^3$ we obtained an upper bound for the peak-to-background ratio of ~60 (Eq. 3).

12. Detection of Fluorescence Excitation by Time-Reversed Light

The time-reversed beam was obtained by reflecting the blank reference beam off the spatial light modulator displaying the measured phase conjugate map. The backscattered fluorescence excited by the time-reversed optical focus was reflected off a dichroic mirror and detected by a single channel PMT fitted with the appropriate bandpass filters (Semrock 650-40, 710-40 or 675-67, for Qtracker 655, Qtracker 705 or DY-521XL long stokes shift NHS-ester dye respectively).

13. Quality Assurance of Digital Optical Phase Conjugation

Because of the dependence of our system on precise alignment, mechanical stability and low drift, we included a parallel sample beam path to asses and assure the performance of our setup on a day-to-day basis. Consisting of ground glass diffusers and an additional observing camera, it was analogous to the setups previously used by our group to demonstrate turbidity suppression by phase conjugation[31].

14. Speckle Decorrelation Time

With the sample beam turned on, we acquired images of the speckle field on the sCMOS camera at a rate of 1 frame/second for 180 seconds. We measured the correlation of the first frame with each subsequent frame and defined the decorrelation time as the time after which the correlation fell below 1-1/e.

II. Theoretical Analysis

1. Description of Complete Time-Reversal

We represent the ultrasound-modulated speckles in the plane of the Ultrasound (US) focus (A) by the electric field $E_A$. Upon further propagation through scattering tissue and free space, the ultrasound-modulated field at the detection plane (B) is $$E'_A = T_{AB} E_A \qquad \text{Eq 4.}$$

where $T_{AB}$ is the complete transmission matrix (with complex transmission values) describing the propagation of $E_A$ from the plane containing the US focus (A) to the detection plane (B). In the case of perfect phase conjugation, where the full solid angle of the scattered wavefront is intercepted and time-reversed, $T_{AB}$ is unitary, lossless and time-symmetric. Thus, the phase conjugated field back at plane A, $E'_A$, is described by $$E'_A = T_{BA}(T_{AB}E_A)^* = T_{BA}T_{BA}^\dagger E^*_A = E^*_A \qquad \text{Eq 5}$$

recovering the ultrasound-modulated field at plane A (where * denotes complex conjugate and † denotes the complex transpose of a matrix). Therefore, theoretically, the electric field of the speckles in the ultrasound focus can be faithfully reconstructed without error when the scattered field is completely time-reversed.

2. Derivation of Peak-to-Background Ratio in Partial Phase Conjugation

Because of the finite etendue of real phase-conjugate mirrors, only a fraction of the scattered wavefront intercepted is time-reversed. As a result, the transmission matrix is no longer unitary. In a random scattering medium, the transmission matrix can instead be approximated by a random matrix with elements independently drawn from a circular complex Gaussian distribution, with $\mu=0$ and $\sigma_{real}=\sigma_{complex}=\sigma^{38}$. Using the framework and methods developed by Vellekoop et. al.[38], we show that a background always exists in the case of partial phase conjugation.

Furthermore, the expected ratio of the peak intensity of the phase conjugate focus and its background can be found. We consider two cases—phase and amplitude time-reversal and phase only time-reversal. The former is relevant to the general case of phase conjugation using photorefractive crystals and digital phase conjugate mirrors with phase and amplitude controls; the latter is specific for the embodiment our system illustrated in FIG. 1c where only the phase of the scattered field is time-reversed.

In both cases, we describe M input channels (speckles) in the ultrasound focus at plane A as a vector with elements, $\hat{E}_m^A$. We let $t_{mn}^{AB}$ be the complex elements of the transmission matrix mapping each of the M input channels (speckles) to the N possible output modes intercepted by the finite area phase conjugate mirror at plane B, where the output channels are represented by the a vector with elements $\hat{E}_n^B$. We consider first a system with only one non-zero input mode (corresponding to a single-mode source). Without the loss of generality, we let this non-zero input mode be $\hat{E}_i^A$. Thus, we obtain $$\hat{E}_n^B = \sum_m^M t_{mn}^{AB} \hat{E}_m^A = t_{1n}^{AB} \hat{E}_1^A \quad \text{Eq 6}$$

Case 1: Phase and Amplitude Time-Reversal

Assuming the phase conjugate mirror has unit reflectivity and invoking the time-symmetric property of the transmission matrix, the phase conjugate, $\hat{E}_1^{A'}$ is $$\hat{E}_1^{A'} = \sum_n^N t_{1n}^{BA}(t_{1n}^{AB}\hat{E}_1^A)^* = (\hat{E}_1^A)^* \sum_n^N |t_{1n}^{AB}|^2 \quad \text{Eq 7}$$

and its intensity is $$\hat{I}_1^{A'} = \left[|\hat{E}_1^A|\sum_n^N |t_{1n}^{AB}|^2\right]^2 = \hat{I}_1^A\left[\sum_n^N |t_{1n}^{AB}|^2\right]^2 = \hat{I}_1^A \alpha^2 \quad \text{Eq 8}$$

Thus, we find that the input speckle considered is reconstructed with some pre-factor, $$\alpha^2 [\Sigma_n^N |t_{1n}^{AB}|^2]^2,$$

determined by the transmission properties of the turbid medium. In a random scattering medium, the ensemble average of $\alpha^2$ can be found by considering the statistics of the circular Gaussian distribution and in so recognizing that a itself follows the Gamma distribution, $\Gamma(N, 2\sigma^2)$. We thus obtain $$<\alpha^2>=4N(N+1)\sigma^4 \quad \text{Eq 9}$$

We will now show that the elements at plane A with zero input will have non-zero phase conjugate intensities, i.e.

$$\hat{I}_m^{A'} < 0 \text{ for } m \neq 1$$

constituting a phase conjugate background. We let the transmission through channel n at plane B back to any input mode $m \neq 1$ at plane A be $t_{mn \neq 1}^{BA}$. Upon playback of the phase conjugate field for $\hat{E}_1^{A'}$, the intensity at plane A where $m \neq 1$ is $$I_m^{A'} = \hat{I}_1^A \left|\sum_n^N t_{n1}^{AB} t_{nm}^{BA}\right|^2 = \hat{I}_1^A \beta^2, \text{ for } m \neq 1 \quad \text{Eq 10}$$

where the ensemble average of $$\beta^2 = |\Sigma_n^N t_{n1}^{AB} t_{nm \neq 1}^{BA}|^2$$

can be found using the statistics of a complex circular Double Gaussian distribution[54].

$$\langle \beta^2 \rangle = \left\langle \left|\sum_n^N t_{n1}^{AB} t_{nm}^{BA}\right|^2 \right\rangle = 4N\sigma^4, \text{ for } m \neq 1 \quad \text{Eq 11}$$

It is clear then that there is a non-zero average background intensity associated with the phase conjugated speckle, and that the ratio of that phase conjugate speckle to its background is:

$$\frac{\langle \alpha^2 \rangle}{\langle \beta^2 \rangle} = N + 1 \quad \text{Eq 12}$$

When there are M non-zero inputs, this result is scaled by $M^{38}$, such that the focal peak-to-background ratio (PBR) is $$PBR_{phase \; \& \; amplitude} = \frac{\langle I'_m \rangle}{\langle I'_o \rangle} = \frac{N+1}{M} \quad \text{Eq 13}$$

Experimentally, N is related to the number of uncorrelated speckles intercepted by the phase conjugate mirror and its upper limit is determined by the number of pixels on the spatial light modulator; M is the number of speckles modulated by the ultrasound and thus decreases as the ultrasound focus decreases.

Case 2: Phase Only Time-Reversal

In the case where a phase only phase conjugate mirror is used, the phase conjugated electric field and intensity of the input speckle, respectively, are $$\hat{E}_1^{A'} = (\hat{E}_1^A)^* \sum_n^N t_{1n}^{BA} \exp[-i \cdot Arg(t_{n1}^{AB})] = \sum_n^N |t_{1n}^{BA}| \quad \text{Eq 14}$$

$$\hat{I}_1^{A'} = \hat{I}_1^A \left[\sum_n^N |t_{1n}^{BA}|\right]^2 \quad \text{Eq 15}$$

and the derivations of $PBR_{phase \; only}$ follows exactly that of Vellekoop et. al. for the case of iterative wavefront optimization to multiple targets through scattering medium[38], obtaining for $N \gg 1$:

$$PBR_{phase \; only} = \frac{\pi}{4}\frac{(N-1)+1}{M} \approx \frac{\pi}{4} \cdot PBR_{phase \; \& \; amplitude} \quad \text{Eq 16}$$

3. Phase Jitter in Acoustic Wave

The technique illustrated in FIG. 1c relies on the detection of 45 MHz ultrasound frequency-shifted light in the presence of a large background of non-shifted light. While the reference beam (equally frequency shifted by 45 MHz) interferes with US-tagged light, interference of the reference beam with the non-shifted light occurs at a beating frequency of 45 MHz (cycle time: 22.2 ns). This beating usually averages out during the much longer integration time of a Complementary Metal Oxide Semiconductor (CMOS) camera. But if the illumination is pulsed, the pulse duration approaches one beating cycle or less and the phase of the beating is locked to the laser trigger output, the interference between the non-shifted beam and the shifted beam may nevertheless be detected. This wouldn't be desirable in the embodiment of FIG. 1c, since a small phase drift between the non-shifted beam and the reference beam would lead to an added artificial signal on the phase map we measure. To ensure that such coherent effects between the non-shifted beam and the frequency-shifted beam are not detected on our camera, we randomly alternate between two trigger delays of a time difference that corresponds to half a 45 MHz beating cycle (11.1 ns or +5.5 ns). A microcontroller randomly chooses a jitter for each laser sync output pulse (at a rate of 20 kHz) and the jitter is added to the trigger delay of ultrasound transducer as well as reference beam AOM. The relative phase between ultrasound-shifted light and the reference beam therefore remains unaffected.

III. Process Steps

Method of Fabrication

Figure 6A:
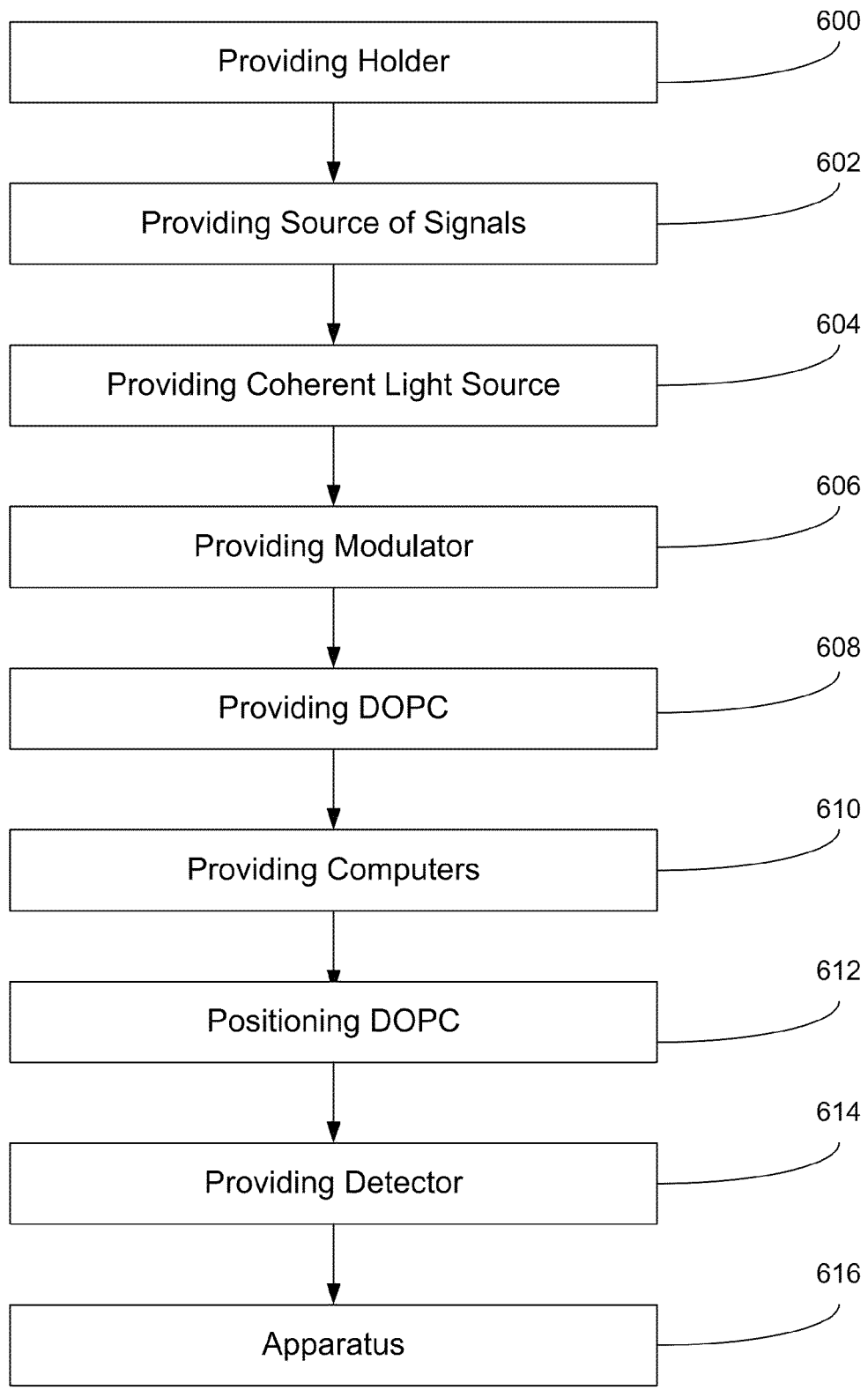
FIG. 6*a-b* illustrate a method of fabricating an apparatus, according to one or more embodiments.

FIG. 6 is a flowchart illustrating a method of fabricating an apparatus for irradiating a scattering medium, in reference to FIG. 1 and according to one or more embodiments of the invention.

Block 600 represents providing a holder, stage, or translation stage, for supporting the scattering medium. The holder can comprise a mechanism to hold the scattering medium (e.g., biological tissue or cells). The holder can be attached to translation stage for moving the scattering medium relative to the UT, laser, DOPC, etc.

Block 602 represents positioning/providing/configuring a source of signals, such that the source of signals can propagate/transmit one or more signals to one or more regions of the scattering medium, wherein the signals have a signal frequency. The signal source can comprise an acoustic or ultrasound wave generator, e.g., an UT transducer generating ultrasound signals or waves.

The step can further comprise providing one or more ultrasound lenses positioned to focus ultrasound waves from the ultrasound transducer, such that the one or more regions comprise one or more ultrasound foci of the ultrasound waves at a depth of at least 2.5 millimeters below a surface of the tissue through which input light (see Block 604) enters the tissue.

Block 604 represents positioning/providing/configuring a coherent light or electromagnetic (EM) radiation source (e.g., laser), such that the coherent light source can propagate/transmit input light or EM radiation through the one or more regions of the scattering medium concurrently with the signals. The positioning/providing/configuring can be such that the signals at least partially modulate the input light into modulated light or EM radiation, as the input light or EM radiation passes through the one or more regions of the scattering medium concurrently with the signals. The step can comprise positioning a first beam splitter to split light from the coherent light source, into the input light and reference light both having the frequency of the light.

Block 606 represents providing/positioning a modulator (e.g., acousto-optic modulator) and/or signal generator to modulate (or frequency shift) the reference light with a signal frequency, into modulated reference light. The signals produced in Block 602 also have the signal frequency and modulate the input light with the same signal frequency.

Block 608 represents providing, fabricating, and/or positioning a Digital Optical Phase Conjugation (DOPC) device such that the DOPC device collects at least a portion of the modulated light, that has exited the scattering medium, as collected modulated light.

The DOPC device can comprise a spatial light modulator (SLM) connected to and imaged on a digital camera 118 or sensor.

The SLM and the sensor can be connected such that the SLM's pixels are aligned with and directly imaged onto the sensor's pixels, such that one SLM pixel is imaged onto one sensor pixel.

The step can comprise positioning one or more second beam splitters, wherein one of the second beam splitters is positioned to combine the modulated reference light and a portion of the modulated light that has exited the scattering medium, such that the modulated reference light and the collected modulated light interfere and form an interference pattern on the camera.

Block 610 represents providing/configuring/programming one or more computers (e.g., any personal computer such as Dell T4100) and/or one or more processors such that the one or more computers/processors:

(i) calculate or obtain time reversed fields or phase conjugated electric fields/wavefronts/phases that are phase conjugates of the collected modulated light's fields/wavefronts/phases. The computer can at least partially digitally phase conjugate one or more electric fields/wavefronts/phases of the collected modulated light, to form the one or more digitally phase conjugated electric fields/wavefronts/phases. The time reversed fields include a desired component that converges back to the one or more regions, and a background component due to incomplete time reversal resulting from only the portion of the encoded light being collected;

(ii) modify (e.g., modify the phases of) the digitally phase conjugated electric fields to produce one or more background fields that at least approximate the background component.

Figure 6B:
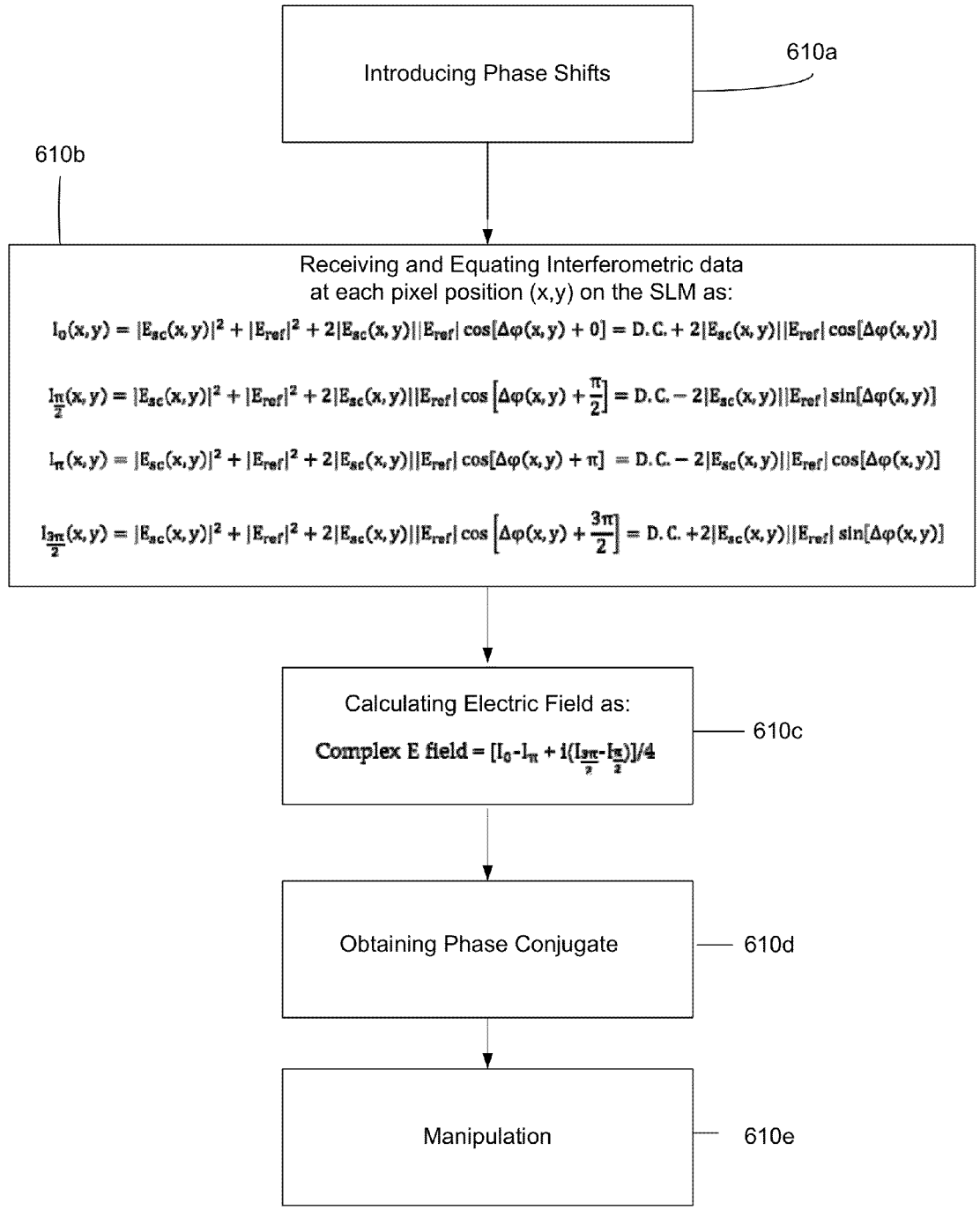

For example, FIG. 6b illustrates how a computer connected to the DOPC can be configured to measure/compute one or more phases of the collected modulated light and compute a phase map of the collected modulated light using the interference pattern, using a digital phase shifting holography technique.

Block 610a illustrates sequentially introducing phase shifts/differences between the modulated reference beam (that is a plane wave) and the modulated light that has exited the scattering medium. The phase shifts can include a sequence of 0, $\pi/2$, $\pi$, and $3\pi/2$ radian shifts between the modulated reference beam and the modulated light (see Section II. 11, phase recording), thereby producing four interference patterns sequentially on the camera. In one embodiment, a microcontroller board (Arduino, Italy; obtained from SparkFun Electronics, USA) connected to an RF switch (Mini-circuits, USA) was programmed to select the appropriate phase for each frame acquired by the sCMOS camera, and an arbitrary function generator (AFG 3252, Tektronix, USA) generated two output signals (one 45 MHz sinusoidal cycle with phase-shift of 0 or $\pi/2$), which were each inverted by a RF 180° power splitter (Mini-circuits, USA) to obtain the four phase-shifted signals. The output signals from the function generator and the RF power splitter can be used to modulate the UT transducer to modulate the input/sample light, thereby introducing the phase shifts between the input/sample light and the reference beam. Alternatively, the output signals from the function generator and RF power splitter can be used in conjunction with an acousto-optic modulator to modulate the reference light, thereby introducing the phase shifts between the input/sample light and the reference beam.

The camera 118 is aligned precisely with the SLM such that when the scattered wavefront of the modulated input/sample light interfered with the frequency-shifted reference beam, the camera 118 measures the phase of the scattered wavefront at the plane of the SLM.

Block 610b represents receiving, in a computer or processor, the interference pattern data for the four phase shifts produced and measured in Block 610a. The computer equates the interferometric data at each pixel position (x,y) on the SLM, where $I_0(x,y)$ is the intensity at pixel (x,y) for zero phase difference, $I_\pi(x,y)$ is the intensity at pixel (x,y) for $\pi$ phase difference, $I_{\pi/2}(x,y)$ is the intensity at pixel (x,y) for $\pi/2$ phase difference, $I_{3\pi/2}(x,y)$ is the intensity at pixel (x,y) for $3\pi/2$ phase difference, $|E_{sc}(x,y)|$ is the electric field amplitude of the scattered beam comprising the modulated light that has exited the scattering medium, $|E_{ref}|$ is the electric field amplitude of the reference light, and $\Delta\phi$ is the phase, at the SLM pixel, of the scattered beam comprising the modulated light. The electric field $E_{sc}$ of the scattered light comprising modulated light, and the electric field $E_{ref}$ of the reference beam can be described as follows:

$$E_{sc}(x,y) = |E_{sc}(x,y)| \exp[j\phi(x,y)]$$

$$E_{ref} = |E_{ref}| \exp[j(\omega)]$$

where the reference light or EM radiation $E_{ref}$ is a plane wave.

Block 610c represents calculating the (e.g., complex) electric field of the modulated light, at the position of the SLM pixels. The complex electric field is calculated as:

$$E = \left[ I_0 - I_\pi + i\left(I\frac{3\pi}{2} - I\frac{\pi}{2}\right) \right] / 4$$

The phase $\Delta\phi$ can be calculated as $\tan^{-1}(\text{Re}(E)/\text{Im}(E))$. Thus, the computer can control the DOPC and phase shifts, to measure the phase map (phase as a function of pixel position x,y on the SLM) using a digital phase shifting holography technique.

Block 610d represents using a computer/processor receiving the complex electric field to compute a phase conjugate map comprising phase conjugates of the phase map. For example, the computer can obtain/calculate the complex conjugate E* of the complex electric field E obtained in Block 610c, and obtain the phase of the complex conjugate electric field using $\tan^{-1}(\text{Re}(E^*)/\text{Im}(E^*))$, thereby obtaining the digital phase conjugate map (phase conjugate as a function of pixel position x,y on the SLM).

Block 610e represents a computer/processor receiving the digital phase conjugate map obtained in Block 610d and modifying the phase conjugates by phase shifting one or more of the phase conjugates by one or more amounts (see e.g., section 1.4). For example, the computer can modify the phase conjugate map by digitally manipulating the phase conjugate map to form a digitally manipulated phase conjugate map. The modifying can produce the background field(s) that approximate the background component.

The laser and the UT transducer can be triggered by a computer to emit light and signals respectively. For example, the computer can comprise randomly alternating between at least two trigger delays between the light, comprising pulsed light, and the signals, comprising pulsed ultrasound waves. The alternating (see section II.3) can counter a phase drift between a background comprising the input light passing through the regions and that is not modulated, and the reference light. The phase drift leads to an undesirable added artificial signal on the phase map.

Block 612 represents providing, programming, and positioning the DOPC device to sequentially irradiate the one or more regions first with the output time reversed light comprising the time reversed fields (comprising desired component that converges to the regions and background component) and then with the light comprising background fields only. One of the second beamsplitters can be positioned to guide the modulated reference light, wherein the reference light reflects off the SLM's display displaying the phase conjugate map and then the digitally manipulated phase conjugate map, to form the output light. Accordingly, dependent on careful pixel to pixel alignment between the camera's pixels and the SLM's pixels, the SLM can faithfully playback a phase conjugate copy of what is recorded on the camera.

Block 614 represents positioning a detector, wherein the detector detects one or more resulting outputs (e.g., fluorescence) that are based on an interaction between the output light and the one or more regions of the scattering medium. The detector detects radiation transmitted from the scattering medium in response to the time reversed fields, to produce a first detected signal, and (2) the detector detects radiation transmitted from the scattering medium in response to the background fields, to produce a second detected signal.

A computer (one of the computers/processors in Block 610 or an additional computer) can be connected to the detector, wherein the computer subtracts the second detected signal from the first detected signal, to obtain an output that at least approximates an interaction between a complete time reversed field, of all of the encoded light's fields, and the scattering medium. The output can have a peak to background ratio of no more than 5.5.

Block 616 represents the end result, an apparatus for irradiating a scattering medium.

In one example, the apparatus comprises (a) an ultrasound transducer (V3330, Olympus NDT[56]); (b) a laser (e.g., Navigator, SpectraPhysics, USA); and (c) a holder for supporting a scattering medium, wherein the ultrasound transducer, the laser, and the holder are connected such that:
  (i) the ultrasound transducer transmits ultrasound waves to one or more foci in one or more regions of the scattering medium;
  (ii) the laser transmits input light to the foci in the one or more regions of the scattering medium concurrently with the ultrasound waves, and
  (iii) the ultrasound waves at least partially frequency shift the input light into modulated light, as the input light passes through the foci concurrently with the ultrasound waves.

The apparatus can further comprise a first beam splitter positioned to split light from the laser, into the input light and reference light both having a frequency of the light.

The DOPC device can comprise a digital programmable spatial light modulator (SLM, e.g., VIS Pluto Holoeye[54]) connected to and imaged (e.g., using a Nikon Micro-Nikkor 105 mm f/2.8 compound lens) onto a digital camera (e.g., pco.edge[55]), wherein:
  (i) the camera is positioned to collect a portion of the modulated light, that has exited the scattering medium, as collected modulated light, and outputs one or more digital signals in response thereto;
  (ii) a computer connected to the DOPC measures one or more phases of the collected modulated light using the digital signals;
  (iii) a computer connected to the DOPC device computes phase conjugate phases that are phase conjugates of the phases
  (iv) a computer connected to the DOPC phase shifts one or more of the phase conjugate phases by one or more amounts to remove the desired component that converges to the foci, to form the background field that approximates the background component;
  (v) the SLM is programmed and positioned to sequentially modulate light first with time reversed fields and then with background fields that at least approximate the background component;
  (vi) the DOPC device is connected to the holder, wherein the DOPC device transmits the output light comprising time reversed fields and then background fields to the one or more foci; and The apparatus can further comprise a detector 128 (e.g., single channel photomultiplier tube) connected to the holder, wherein the detector detects radiation transmitted from the scattering medium in response to the output light.

In one embodiment, the camera comprises an analog/digital dynamic range of at least 16 bits; the SLM comprises a resolution of at least 1920 by 1080 pixels and an input frame rate of at least 60 Hz; and he DOPC device outputs the output light having the time reversed fields with a power having a gain of at least $10^\circ$ as compared to a power of the modulated light collected by the DOPC.

A response time of the apparatus can be faster than 6.7 seconds, or faster than a decorrelation time of the scattering medium, wherein the response time is a time between the encoding and the irradiating with the background fields that produces the second detected signals.

In another embodiment, the response time is a time between the ultrasound waves at least partially frequency shifting the input light into modulated light and the detector detecting radiation transmitted from the scattering medium in response to the background fields.

The modifying and a focus of the signals can be such that the output light's lateral resolution is at most 36 μm by 52 μm, and the output light's axial resolution is at most 657 μm.

Method of Irradiating a Scattering Medium

Figure 7:
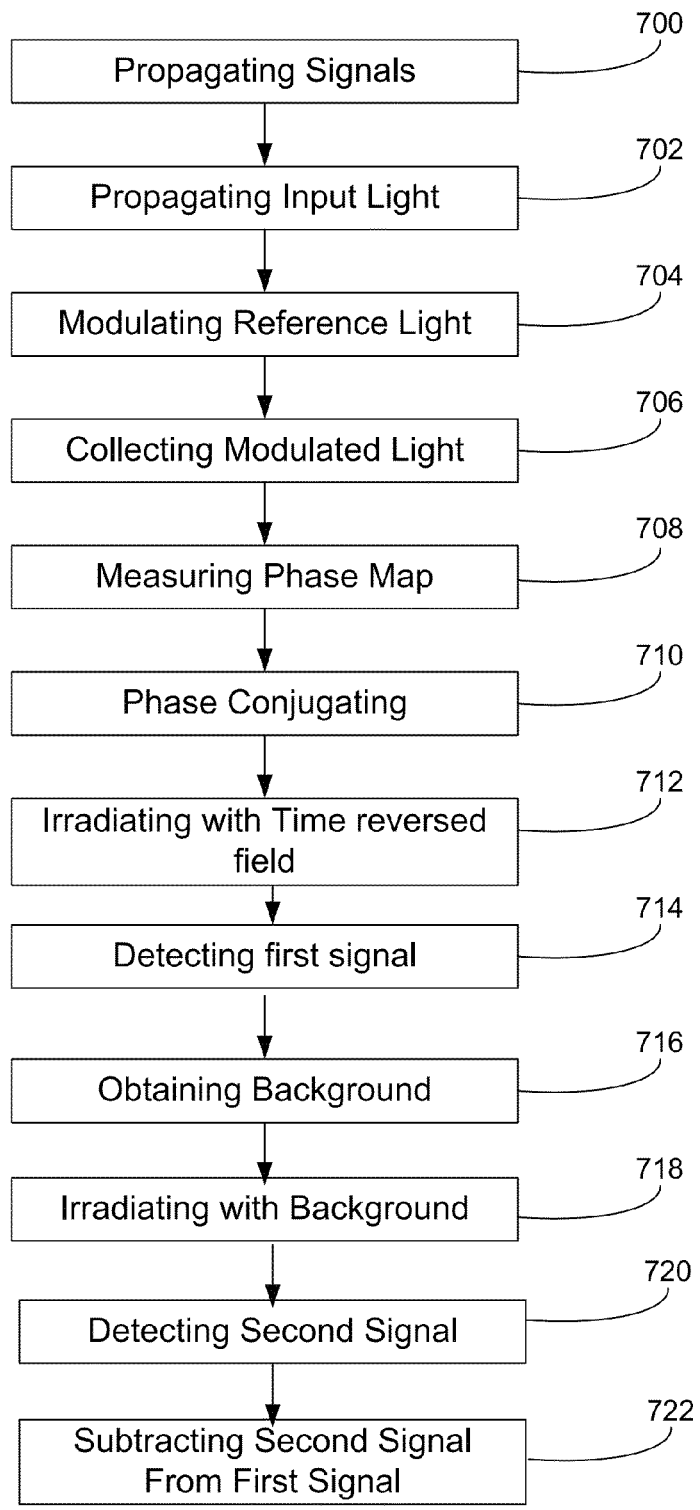
FIG. 7 illustrates a method of irradiating a scattering medium, according to one or more embodiments.

FIG. 7 represents a method for irradiating a scattering medium, according to one or more embodiments.

Block 700 represents propagating/transmitting one or more signals from a source of signals and to one or more regions of the scattering medium, wherein the signals have a signal frequency.

For example, the scattering medium can be tissue and the regions can be positioned at a depth of at least 2.5 millimeters below a surface of the tissue. One or more of the signals can comprise one or more acoustic or ultrasound waves generated by one or more acoustic wave sources (e.g., UT transducer). The ultrasound waves can be focused such that the one or more regions comprise one or more ultrasound foci of the ultrasound waves.

Block 702 represents propagating/transmitting input light from a coherent light source/laser and through the one or more regions of the scattering medium concurrently with the signals, wherein the signals at least partially modulate the input light into modulated light, as the input light passes through the one or more regions of the scattering medium concurrently with the signals. The step can comprise splitting light from a laser and using a beamsplitter, into the input light and reference light both having the frequency of the light.

Blocks 700-702 enable encoding light, in one or more regions of a scattering medium, with a signal.

Block 704 represents modulating, in a modulator, the reference light with the signal frequency, to form modulated reference light (i.e., wherein the signals modulate the input light with the same signal frequency).

Block 706 represents collecting, in a digital optical phase conjugation (DOPC) device, at least a portion of the encoded/modulated light that has exited the scattering medium, as collected modulated light. The step can comprise combining the modulated reference light and a portion of the modulated light that has exited the scattering medium, such that the reference light and the collected modulated light interfere and form an interference pattern on a camera in the DOPC.

Block 708 represents measuring a phase map or phases of the collected modulated light. The step can comprise measuring the phase map or phases of the collected modulated light using the interference pattern and a computer (e.g., using digital phase shifting holography).

Block 710 represents producing, digitally computing, or obtaining time reversed/phase conjugate fields/phases that are phase conjugates of the collected modulated light's fields/phases.

The step can comprise at least partially digitally phase conjugating one or more electric fields and/or wavefronts E, W and/or phases of the collected modulated light, to form one or more digitally phase conjugated wavefronts or electric fields E*, W*. The phase conjugating can comprise shaping or modifying a phase and/or amplitude of the collected modulated light, to produce one or more wavefronts/electric fields that are one or more phase conjugates of one or more wavefronts/electric fields of the collected modulated light. In one or more embodiments, only the phase is shaped or modified to produce the phase conjugate.

The at least partially digitally phase conjugating can comprise digitally phase conjugating the phase map (e.g., in a computer) to produce a phase conjugate map.

Block 712 represents irradiating the scattering medium with the time reversed fields, wherein the time reversed fields include a desired component that converges back to the one or more regions, and a background component due to incomplete time reversal resulting from only the portion of the encoded light being collected. The step can comprise displaying, on the SLM's display placed at an image plane of the camera, the phase conjugate map; and guiding (e.g., using a beamsplitter) the reference light, wherein the reference light reflects off the SLM display displaying the phase conjugate map to form the time reversed light comprising the time reversed fields.

For example, the output time reversed light/fields can be used to excite fluorescent agents in the one or more regions, thereby producing fluorescence.

For example, the time reversed light/fields can be used to excite fluorescent agents or photosensitizing agents in the one or more regions, wherein the excited fluorescent agents or photosensitizing agents induce biochemical reactions in the one or more regions of the scattering medium.

Block 714 represents detecting, on a detector, output radiation based on an interaction between the time reversed fields and the scattering medium, to produce a first detected signal.

Block 716 represents modifying the phase conjugate fields to form modified phase conjugate fields. The modifying can modify the digital phase conjugate fields to produce the background fields that estimate, approximate, at least approximate, or replicate the background component. The modifying can comprise digital manipulation of the phase conjugate map in a computer.

The digital manipulation can comprise digitally shifting the phase conjugate map by a plurality of pixels of the SLM.

The digital manipulation can comprise dividing the phase conjugate map into sub-regions and phase-shifting every other sub-region by a plurality of degrees.

The modifying can phase shifting one or more of the phase conjugate phases by one or more amounts to remove the desired component that converges to the foci.

Block 718 represents irradiating the scattering medium with the one or more background fields that at least approximate the background component. The step can comprise displaying, on the SLM's display placed at an image plane of the camera, the digitally manipulated phase conjugate map; and guiding (e.g., using a beamsplitter) the reference light, wherein the reference light reflects off the SLM display displaying the digitally manipulated phase conjugate map to form the background light comprising the background fields.

Block 720 represents detecting, on a detector, output radiation based on an interaction between the background fields and the scattering medium, to produce a second detected signal.

Block 722 represents subtracting, in a computer, the second detected signal from the first detected signal, to obtain an output that at least approximates an interaction between a complete time reversed field, of all of the encoded light's fields, and the scattering medium.

Accordingly, the irradiating with the time reversed fields/ background fields can image the scattering medium. For example, the detecting and subtracting can be used to construct an image the scattering medium, using the fluorescence caused by the irradiation with the time reversed light corrected for/adjusted by/minus the background. In one or more embodiments, the scattering medium can have a scattering coefficient $\mu_s$ of at least 30 mm$^{-1}$.

Accordingly, one or more embodiments of FIG. 7 can 1) play back (irradiate the scattering medium with) the phase conjugate field that contains a background due to incomplete time reversal (e.g., focus+background); 2) detect signals excited by this phase conjugate field; 3) modify the phase conjugate field to obtain the field that estimates the background field or results in an approximation of the background field; 4) irradiate with the modified field produced in 3); 4) detect signals excited by the modified field; and 5) subtract signal from 4) from signals in 2) to obtain signal from the phase conjugate focus.

IV. Hardware Environment

Figure 8:
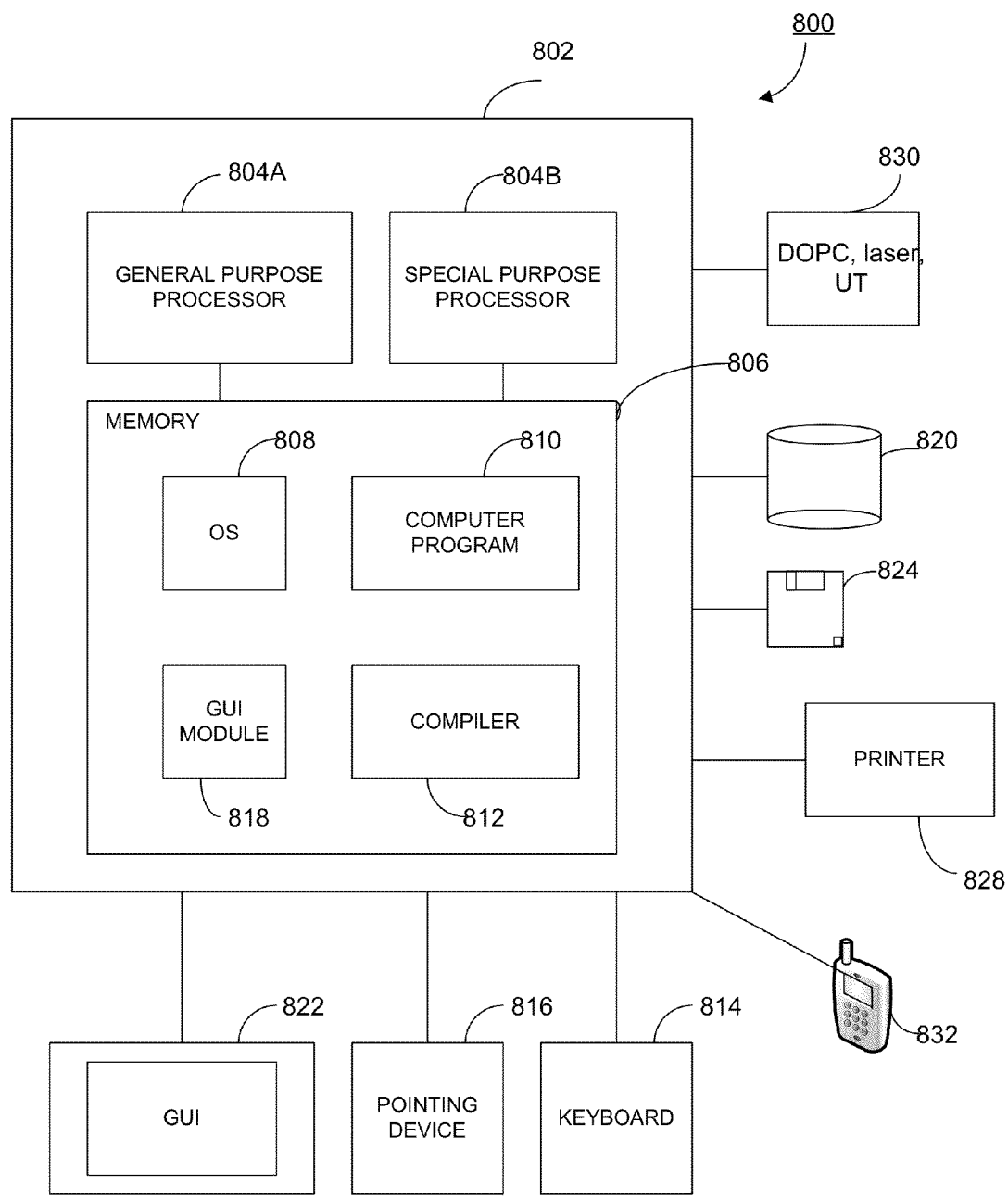
FIG. 8 is an exemplary hardware and software environment used to implement one or more embodiments of the processing, control, encryption, transmitting, or receiving functions of the invention.

FIG. 8 is an exemplary hardware and software environment 800 used to implement one or more embodiments of the processing, control, encryption, transmitting, or receiving functions of the invention. The hardware and software environment includes a computer 802 and may include peripherals. Computer 802 may be a user/client computer, server computer, or may be a database computer. The computer 802 comprises a general purpose hardware processor 804A and/or a special purpose hardware processor 804B (hereinafter alternatively collectively referred to as processor 804) and a memory 806, such as random access memory (RAM). The computer 802 may be coupled to, and/or integrated with, other devices, including input/output (I/O) devices such as a keyboard 814, a cursor control device 816 (e.g., a mouse, a pointing device, pen and tablet, touch screen, multi-touch device, etc.) and a printer 828. In one or more embodiments, computer 802 may be coupled to, or may comprise, a portable or media viewing/listening device 832 (e.g., an MP3 player, iPod™, Nook™, portable digital video player, cellular device, personal digital assistant, etc.). In yet another embodiment, the computer 802 may comprise a multi-touch device, mobile phone, gaming system, internet enabled television, television set top box, or other internet enabled device executing on various platforms and operating systems.

In one embodiment, the computer 802 operates by the general purpose processor 804A performing instructions defined by the computer program 810 under control of an operating system 808. The computer program 810 and/or the operating system 808 may be stored in the memory 806 and may interface with the user and/or other devices to accept input and commands and, based on such input and commands and the instructions defined by the computer program 810 and operating system 808, to provide output and results.

Output/results may be presented on the display 822 or provided to another device for presentation or further processing or action. In one embodiment, the display 822 comprises a liquid crystal display (LCD) having a plurality of separately addressable liquid crystals. Alternatively, the display 822 may comprise a light emitting diode (LED) display having clusters of red, green and blue diodes driven together to form full-color pixels. Each liquid crystal or pixel of the display 822 changes to an opaque or translucent state to form a part of the image on the display in response to the data or information generated by the processor 804 from the application of the instructions of the computer program 810 and/or operating system 808 to the input and commands. The image may be provided through a graphical user interface (GUI) module 818. Although the GUI module 818 is depicted as a separate module, the instructions performing the GUI functions can be resident or distributed in the operating system 808, the computer program 810, or implemented with special purpose memory and processors.

In one or more embodiments, the display 822 is integrated with/into the computer 802 and comprises a multi-touch device having a touch sensing surface (e.g., track pod or touch screen) with the ability to recognize the presence of two or more points of contact with the surface. Examples of multi-touch devices include mobile devices or smartphones (e.g., iPhone™, Nexus S™, Droid™ devices, etc.), tablet computers (e.g., iPad™, HP Touchpad™), portable/handheld game/music/video player/console devices (e.g., iPod Touch™, MP3 players, Nintendo 3DS™, PlayStation Portable™, etc.), touch tables, and walls (e.g., where an image is projected through acrylic and/or glass, and the image is then backlit with LEDs).

Some or all of the operations performed by the computer 802 according to the computer program 810 instructions may be implemented in a special purpose processor 804B. In this embodiment, the some or all of the computer program 810 instructions may be implemented via firmware instructions stored in a read only memory (ROM), a programmable read only memory (PROM) or flash memory within the special purpose processor 804B or in memory 806. The special purpose processor 804B may also be hardwired through circuit design to perform some or all of the operations to implement the present invention. Further, the special purpose processor 804B may be a hybrid processor, which includes dedicated circuitry for performing a subset of functions, and other circuits for performing more general functions such as responding to computer program 810 instructions. In one embodiment, the special purpose processor 804B is an application specific integrated circuit (ASIC).

The computer 802 may also implement a compiler 812 that allows an application or computer program 810 written in a programming language such as COBOL, Pascal, C++, FORTRAN, or other language to be translated into processor 804 readable code. Alternatively, the compiler 812 may be an interpreter that executes instructions/source code directly, translates source code into an intermediate representation that is executed, or that executes stored precompiled code. Such source code may be written in a variety of programming languages such as Java™, Perl™, Basic™, etc. After completion, the application or computer program 810 accesses and manipulates data accepted from I/O devices and stored in the memory 806 of the computer 802 using the relationships and logic that were generated using the compiler 812.

The computer 802 also optionally comprises an external communication device such as a modem, satellite link, Ethernet card, or other device for accepting input from, and providing output to, other computers 802.

In one embodiment, instructions implementing the operating system 808, the computer program 810, and the compiler 812 are tangibly embodied in a non-transient computer-readable medium, e.g., data storage device 820, which could include one or more fixed or removable data storage devices, such as a zip drive, floppy disc drive 824, hard drive, CD-ROM drive, tape drive, etc. Further, the operating system 808 and the computer program 810 are comprised of computer program 810 instructions which, when accessed, read and executed by the computer 802, cause the computer 802 to perform the steps necessary to implement and/or use the present invention or to load the program of instructions into a memory 806, thus creating a special purpose data structure causing the computer 802 to operate as a specially programmed computer executing the method steps described herein. Computer program 810 and/or operating instructions may also be tangibly embodied in memory 806, thereby making a computer program product or article of manufacture according to the invention. As such, the terms "article of manufacture," "program storage device," and "computer program product," as used herein, are intended to encompass a computer program accessible from any computer readable device or media.

Of course, those skilled in the art will recognize that any combination of the above components, or any number of different components, peripherals, and other devices, may be used with the computer 802.

For example, the processors 804a or 804b may execute algorithm/program 810 in the computers of block 610, or as necessary to implement to steps of Blocks 700-722. The apparatus can further comprise one or more computer readable storage media encoded with one or more computer program instructions which when accessed by the computers cause the computers to load the program instructions to a memory therein creating a special purpose data structure causing the computers to operate as a specially programmed computer, executing the functions of computing the phase map, phase conjugating the phase map, and digitally manipulating the phase maps, and triggering delays.

Figure 9:
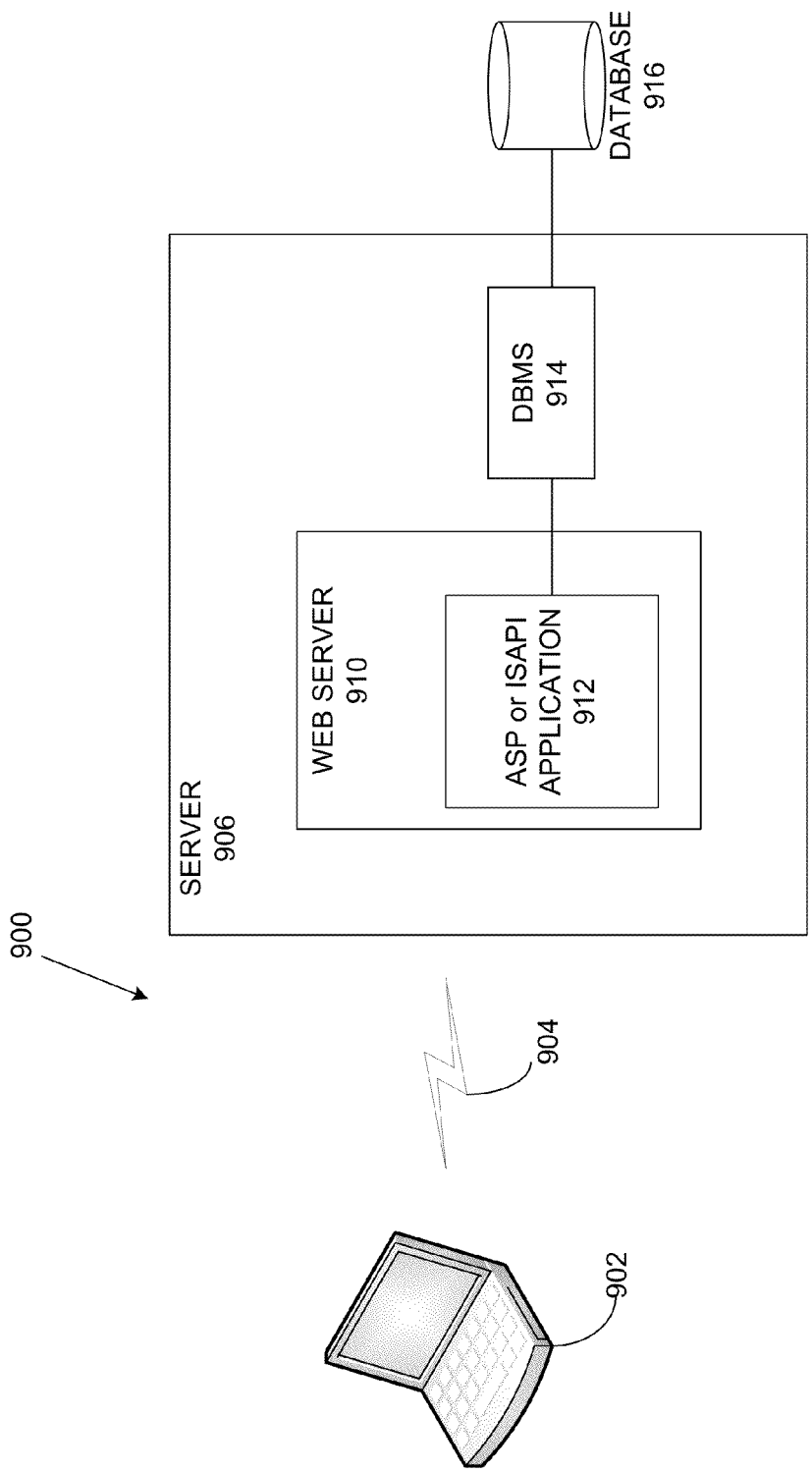
FIG. 9 schematically illustrates a typical distributed computer system using a network to connect client computers to server computers.

FIG. 9 schematically illustrates a typical distributed computer system 900 using a network 904 to connect client computers 902 to server computers 906. A typical combination of resources may include a network 904 comprising the Internet, LANs (local area networks), WANs (wide area networks), SNA (systems network architecture) networks, or the like, clients 902 that are personal computers or workstations (as set forth in FIG. 8), and servers 906 that are personal computers, workstations, minicomputers, or mainframes (as set forth in FIG. 8). However, it may be noted that different networks such as a cellular network (e.g., GSM [global system for mobile communications] or otherwise), a satellite based network, or any other type of network may be used to connect clients 902 and servers 906 in accordance with embodiments of the invention.

A network 904 such as the Internet connects clients 902 to server computers 906. Network 904 may utilize ethernet, coaxial cable, wireless communications, radio frequency (RF), etc. to connect and provide the communication between clients 902 and servers 906. Clients 902 may execute a client application or web browser and communicate with server computers 906 executing web servers 910. Such a web browser is typically a program such as MICROSOFT INTERNET EXPLORER™, MOZILLA FIREFOX™, OPERA™, APPLE SAFARI™, etc. Further, the software executing on clients 902 may be downloaded from server computer 906 to client computers 902 and installed as a plug-in or ACTIVEX™ control of a web browser. Accordingly, clients 902 may utilize ACTIVEX™ components/component object model (COM) or distributed COM (DCOM) components to provide a user interface on a display of client 902. The web server 910 is typically a program such as MICROSOFT'S INTERNET INFORMATION SERVER™.

Web server 910 may host an Active Server Page (ASP) or Internet Server Application Programming Interface (ISAPI) application 912, which may be executing scripts. The scripts invoke objects that execute business logic (referred to as business objects). The business objects then manipulate data in database 916 through a database management system (DBMS) 914. Alternatively, database 916 may be part of, or connected directly to, client 902 instead of communicating/obtaining the information from database 916 across network 904. When a developer encapsulates the business functionality into objects, the system may be referred to as a component object model (COM) system. Accordingly, the scripts executing on web server 910 (and/or application 912) invoke COM objects that implement the business logic. Further, server 906 may utilize MICROSOFT'S™ Transaction Server (MTS) to access required data stored in database 916 via an interface such as ADO (Active Data Objects), OLE DB (Object Linking and Embedding DataBase), or ODBC (Open DataBase Connectivity).

Generally, these components 900-916 all comprise logic and/or data that is embodied in/or retrievable from device, medium, signal, or carrier, e.g., a data storage device, a data communications device, a remote computer or device coupled to the computer via a network or via another data communications device, etc. Moreover, this logic and/or data, when read, executed, and/or interpreted, results in the steps necessary to implement and/or use the present invention being performed.

Although the terms "user computer", "client computer", and/or "server computer" are referred to herein, it is understood that such computers 902 and 906 may be interchangeable and may further include thin client devices with limited or full processing capabilities, portable devices such as cell phones, notebook computers, pocket computers, multi-touch devices, and/or any other devices with suitable processing, communication, and input/output capability.

Of course, those skilled in the art will recognize that any combination of the above components, or any number of different components, peripherals, and other devices, may be used with computers 902 and 906.

Software Embodiment Overview

Embodiments of the invention are implemented as a software application on a client 902 or server computer 906. Further, as described above, the client 902 or server computer 906 may comprise a thin client device or a portable device that has a multi-touch-based display.

Further Considerations

Focal fluorescence imaging in biological tissues beyond one transport mean free path is one of the most challenging frontiers in biomedical optics. In this study, we provide the first demonstration of focal fluorescence imaging in the diffusive regime with time-reversal of ultrasound-tagged light. We implemented a digital optical phase conjugation (DOPC) system with high gain to directly observe the time-reversed optical focus and the accompanying phase-conjugate background. We took advantage of the capabilities of the DOPC to digitally manipulate the phase conjugate map to dynamically estimate and subtract the fluorescence contribution of the phase-conjugate background that would otherwise obscure the focal fluorescence signal. Using this technique, we characterized the point-spread function of the system of FIG. 1c as having an anisotropic lateral resolution of 34 µm by 52 µm and an axial resolution of 657 µm. Furthermore, we illustrated the capabilities of our method by successfully imaging fluorescent objects 2.5 mm deep in er vivo tissue, equivalent to about 75 scattering mean free paths[31].

As confirmed by our results, the imaging resolution perpendicular to the axis of light propagation is determined by the ultrasound focal volume. The system's resolution can therefore be improved by utilizing an ultrasound transducer with a higher central frequency and a higher numerical aperture. However, some expected tradeoffs should be noted. Higher frequency ultrasound is more strongly attenuated in biological tissues[44], thus reducing the practical focusing depth of the ultrasound. Additionally, a smaller modulation volume would further diminish the population of the frequency-shifted light and increase the challenge of detecting a small signal on top of a large background during phase measurement. However, these issues can be addressed by the development of faster, higher dynamic-range cameras, and with advanced filtering methods[45,46]. The point-spread-function along the axis of light propagation is limited by the angular spread of the focused light cone. Since the angular spread is a function of illumination geometry and tissue scattering, the resolution could be improved by using high numerical aperture illumination or—counter-intuitively—by imaging thicker, more scattering samples. Finally, the resolution along the axis of light propagation could further be improved by taking advantage of multiphoton excitation.

We estimate that at the plane of the time-reversed focus, less than 1% of the energy is within the focus. This means that 99% of the remaining energy is spread over the diffuse background, which if uncorrected can obscure focal fluorescence signal. In inhomogeneous fluorescent samples, we showed that dynamic background subtraction effectively uncouples the focal fluorescence signal from that excited by the background. In some applications like photodynamic therapy, where the goal is to deliver more light into the focus, a further increase in peak-to-background ratio may be desirable. There are two ways to achieve a higher peak-to-background ratio. First, the number of optical modes (N) intercepted by the DOPC can be increased by increasing the number of pixels on the SLM. Second, the number of optical modes in the ultrasound focus (M) can be decreased by decreasing the size of the ultrasound focus.

Because our methods are based on optical time-reversal, it relies on mechanical stability of the sample. The acquisition cycle per pixel should therefore be faster or on the same order of magnitude as the speckle decorrelation of the tissue. This condition is easily met in er vivo experiments: our current pixel acquisition time (6.7 s) was shorter than the decorrelation time of the sample (41 s). For in vivo applications, decorrelation times are typically much faster: published values range from millisecond scale[47,48,49] to second scale[50], depending on tissue type and immobilization strategies. For such applications, the pixel acquisition time would have to be reduced accordingly. We anticipate that this will ultimately be possible with the use of faster spatial light modulators[51], and the continuing development of faster, higher dynamic range cameras. In all our experiments, the irradiance of the laser beam at the sample was less than 10 mW/mm². The laser power would have to be decreased, or the diameter of the beam increased, to meet clinical safety standards (2 mW/mm²). Taken together, such improvements would ultimately enable a wide range of in vivo applications, including molecular imaging, early cancer diagnosis, photodynamic therapy and targeted excitation of optogenetic tools in deep tissues.

Further information on one or more embodiments of the invention can be found Wang, Y. M., B. Judkewitz, et al. (2012). *Nat Commun* 3: 928[57].

REFERENCES

The following references are incorporated by reference herein.

1. Denk, W., Strickler, J. & Webb, W. Two-photon laser scanning fluorescence microscopy. *Science* 248, 73-76 (1990).
2. Helmchen, F. & Denk, W. Deep tissue two-photon microscopy. *Nat Meth* 2, 932-940 (2005).
3. Minsky, M. Microscopy Apparatus. (USA, 1961).
4. Huang, D., et al. Optical coherence tomography. *Science* 254, 1178-1181 (1991).
5. Ntziachristos, V. Going deeper than microscopy: the optical imaging frontier in biology. *Nat Meth* 7, 603-614 (2010).
6. Ntziachristos, V., Ripoll, J., Wang, L. V. & Weissleder, R. Looking and listening to light: the evolution of whole-body photonic imaging. *Nat Biotech* 23, 313-320 (2005).
7. Lichtman, J. W. & Conchello, J.-A. Fluorescence microscopy. *Nat Meth* 2, 910-919 (2005).
8. Vellekoop, I. M., LagendijkA & Mosk, A. P. Exploiting disorder for perfect focusing. *Nat Photon* 4, 320-322 (2010).
9. van Putten, E. G., et al. Scattering Lens Resolves Sub-100 nm Structures with Visible Light. *Physical Review Letters* 106, 193905 (2011).
10. Hsieh, C. L., Pu, Y., Grange, R. & Psaltis, D. Digital phase conjugation of second harmonic radiation emitted by nanoparticles in turbid media. *Optics Express* 18, 12283-12290.
11. Popoff, S., Lerosey, G., Fink, M., Boccara, A. C. & Gigan, S. Image transmission through an opaque material. *Nat Commun* 1, 81 (2010).
12. Katz, O., Small, E., Bromberg, Y. & Silberberg, Y. Focusing and compression of ultrashort pulses through scattering media. *Nat Photon* 5, 372-377 (2011).
13. Mudry, E., Le Moal, E., Ferrand, P., Chaumet, P. C. & Sentenac, A. Isotropic Diffraction-Limited Focusing Using a Single Objective Lens. *Physical Review Letters* 105, 203903 (2010).
14. McCabe, D. J., et al. Spatio-temporal focusing of an ultrafast pulse through a multiply scattering medium. *Nat Commun* 2, 447 (2011).
15. Katz, O., Small, E., Bromberg, Y. & Silberberg, Y. Focusing and compression of ultrashort pulses through scattering media. *Nat Photonics* 5, 372-377 (2011).
16. Yaqoob, Z., Psaltis, D., Feld, M. S. & Yang, C. H. Optical phase conjugation for turbidity suppression in biological samples. *Nat Photonics* 2, 110-115 (2008).
17. Leith, E. N. & Upatniek. J. Holographic Imagery Through Diffusing Media. *Journal of the Optical Society of America* 56, 523-& (1966).
18. Goodman, J. W., Huntley, W. H., Jackson, D. W. & Lehmann, M. Wavefront-Reconstruction Imaging Through Random Media. *Applied Physics Letters* 8, 311-& (1966).
19. Davies, R. & Kasper, M. Adaptive Optics for Astronomy. *Annual Review of Astronomy and Astrophysics* 50, 1-47 (2012).
20. Zawadzki, R. J., et al. Adaptive-optics optical coherence tomography for high-resolution and high-speed 3D retinal in vivo imaging. *Optics Express* 13, 8532-8546 (2005).
21. Xu, X., Liu, H. & Wang, L. V. Time-reversed ultrasonically encoded optical focusing into scattering media. *Nat Photonics* 5, 154-157 (2011).
22. Yariv, A. Phase conjugate optics and real-time holography. *Quantum Electronics, IEEE Journal of* 14, 650-660 (1978).
23. Mahan, G. D., Engler, W. E., Tiemann, J. J. & Uzgiris, E. Ultrasonic Tagging of Light: Theory. *Proceedings of the National Academy of Sciences of the United States of America* 95, 14015-14019 (1998).
24. Liu, H., Xu, X., Lai, P. & Wang, L. V. Time-reversed ultrasonically encoded optical focusing into tissue-mim- 25. Lai, P., Xu, X., Liu, H., Suzuki, Y. & Wang, L. V. Reflection-mode time-reversed ultrasonically encoded optical focusing into turbid media. *Journal of biomedical optics* 16, 080505 (2011).
26. Kothapalli, S. R. & Wang, L. H. V. Ultrasound-modulated optical microscopy. *Journal of biomedical optics* 13(2008).
27. Feinberg, J., Heiman, D., Tanguay, A. R. & Hellwarth, R. W. Photorefractive effects and light-induced charge migration in barium titanate. *Journal of Applied Physics* 51, 1297-1305 (1980).
28. Gunter, P. & Huignard, J. P. *Photorefractive Materials And Their Applications*. 1 Basic Effects, (Springer, 2006).
29. Vellekoop, I. M. & Mosk, A. P. Universal Optimal Transmission of Light Through Disordered Materials. *Physical Review Letters* 101, 120601 (2008).
30. Gu, C. & Yeh, P. C. Partial phase conjugation, fidelity, and reciprocity. *Optics Communications* 107, 353-357 (1994).
31. McDowell, E. J., et al. Turbidity suppression from the ballistic to the diffusive regime in biological tissues using optical phase conjugation. *Journal of biomedical optics* 15, 025004 (2010).
32. Cui, M. & Yang, C. H. Implementation of a digital optical phase conjugation system and its application to study the robustness of turbidity suppression by phase conjugation. *Optics Express* 18, 3444-3455 (2010).
33. Atlan, M., Forget, B. C., Ramaz, F., Boccara, A. C. & Gross, M. Pulsed acousto-optic imaging in dynamic scattering media with heterodyne parallel speckle detection. *Optics Letters* 30, 1360-1362 (2005).
34. Feinberg, J. & Hellwarth, R. W. Phase-conjugating mirror with continuous-wave gain. *Optics Letters* 5, 519-521 (1980).
35. Lanzerotti, M. Y., Schirmer, R. W. & Gaeta, A. L. High-reflectivity, wide-bandwidth optical phase conjugation via four-wave mixing in potassium vapor. *Applied Physics Letters* 69, 1199-1201 (1996).
36. Tschudi, T., et al. Image amplification by two- and four-wave mixing in BaTiO3 photorefractive crystals. *Quantum Electronics, IEEE Journal of* 22, 1493-1502 (1986).
37. Yamaguchi, I. & Zhang, T. Phase-shifting digital holography. *Opt. Lett.* 22, 1268-1270 (1997).
38. Vellekoop, I. M. Controlling the propagation of light in disordered scattering media. *University of Twente Thesis*, 1-142 (2008).
39. Vellekoop, I. M. & Mosk, A. P. Focusing coherent light through opaque strongly scattering media. *Optics Letters* 32, 2309-2311 (2007).
40. Leray, A. & Mertz, J. Rejection of two-photon fluorescence background in thick tissue by differential aberration imaging. *Optics Express* 14, 10565-10573 (2006).
41. Leray, A., Lillis, K. & Mertz, J. Enhanced background rejection in thick tissue with differential-aberration two-photon microscopy. *Biophysical Journal* 94, 1449-1458 (2008).
42. Cheong, W. F., Prahl, S. A. & Welch, A. J. A Review of the Optical Properties of Biological Tissues. *Ieee Journal of Quantum Electronics* 26, 2166-2185 (1990).
43. Zell, K., Sperl, J. I., Vogel, M. W., Niessner, R. & Haisch, C. Acoustical properties of selected tissue phantom materials for ultrasound imaging. *Physics in Medicine and Biology* 52, N475-N484 (2007).
44. Goss, S. A., Frizzell, L. A. & Dunn, F. Ultrasonic absorption and attenuation in mammalian tissues. *Ultrasound in Medicine & Biology* 5, 181-186 (1979).
45. Li, Y., Hemmer, P., Kim, C., Zhang, H. & Wang, L. V. Detection of ultrasound-modulated diffuse photons using spectral-hole burning. *Optics Express* 16, 14862-14874 (2008).
46. Gross, M., et al. Detection of the tagged or untagged photons in acousto-optic imaging of thick highly scattering media by photorefractive adaptive holography. *Eur Phys J E* 28, 173-182 (2009).
47. Draijer, M., Hondebrink, E., van Leeuwen, T. & Steenbergen, W. Review of laser speckle contrast techniques for visualizing tissue perfusion. *Lasers in Medical Science* 24, 639-651 (2009).
48. Hajjarian, Z., Xi, J., Jaffer, F. A., Tearney, G. J. & Nadkarni, S. K. Intravascular laser speckle imaging catheter for the mechanical evaluation of the arterial wall. *Journal of biomedical optics* 16(2011).
49. Lev, A. & Sfez, B. In vivo demonstration of the ultrasound-modulated light technique. *Journal of the Optical Society of America. A, Optics, image science, and vision* 20, 2347-2354 (2003).
50. Cui, M., McDowell, E. J. & Yang, C. An in vivo study of turbidity suppression by optical phase conjugation (TSOPC) on rabbit ear. *Optics Express* 18, 25-30 (2010).
51. Conkey, D. B., Caravaca-Aguirre, A. M. & Piestun, R. High-speed scattering medium characterization with application to focusing light through turbid media. *Optics Express* 20, 1733-1740 (2012).
52. Beningo, K. A. & Wang, Y. L. Fc-receptor-mediated phagocytosis is regulated by mechanical properties of the target. *Journal of Cell Science* 115, 849-856 (2002).
53. Kelm, J. M., Timmins, N. E., Brown, C. J., Fussenegger, M. & Nielsen, L. K. Method for generation of homogeneous multicellular tumor spheroids applicable to a wide variety of cell types. *Biotechnology and Bioengineering* 83, 173-180 (2003).
54. http://holoeye.com/spatial-light-modulators/slm-pluto-phase-only/
55. http://www.pco.de/categories/scmos-cameras/pcoedge/
56. http://shop.olympus-ims.com/en/shop/item/269-productId.570437674_269-catId.562036984.html
57. Wang, Y. M., B. Judkewitz, et al. (2012). *Nat Commun* 3: 928; DOI 10:1038/ncomms1925, entitled "Deep-tissue focal fluorescence imaging with digitally time-reversed ultrasound-encoded light."

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A method of irradiating a scattering medium, comprising:
   encoding light with one or more signals, in one or more regions of a scattering medium, to form encoded light;
   collecting a portion of the encoded light, comprising one or more encoded fields, in a digital optical phase conjugation (DOPC) device comprising a spatial light modulator (SLM) connected to a camera;
   producing, in the DOPC device, one or more time reversed fields that are phase conjugates of the encoded fields;

irradiating the scattering medium with the time reversed fields, wherein the time reversed fields include a desired component that converges back to the one or more regions, and a background component due to incomplete time reversal resulting from only the portion of the encoded light being collected;

detecting, on a detector, first output radiation based on an interaction between the time reversed fields and the scattering medium, to produce a first detected signal;

irradiating the scattering medium with one or more background fields that at least approximate the background component;

detecting, on a detector, second output radiation based on an interaction between the background fields and the scattering medium, to produce a second detected signal; and subtracting, in a computer, the second detected signal from the first detected signal, to obtain an output that at least approximates an interaction between a complete time reversed light field, comprising phase conjugates of all of the encoded light's fields, and the scattering medium.

2. The method of claim 1, further comprising:

transmitting one or more of the signals from a source of signals and to the one or more regions of the scattering medium;

transmitting input light from a laser and through the one or more regions of the scattering medium concurrently with the signals, wherein the signals at least partially modulate the input light into modulated light to form the encoded light;

collecting, in the DOPC device, a portion of the modulated light transmitted out of scattering medium, as collected modulated light;

computing one or more digital phase conjugate fields that are phase conjugates of the collected modulated light's fields;

irradiating the one or more regions with the time reversed fields comprising the digital phase conjugate fields; and modifying the digital phase conjugate fields to produce the background fields.

3. The method of claim 2, further comprising:

measuring a phase map of the collected modulated light, wherein:
  the computing comprises digitally phase conjugating the phase map to produce a phase conjugate map; and
  the modifying comprises digital manipulation of the phase conjugate map in a computer.

4. The method of claim 3, wherein the DOPC device comprises the spatial light modulator (SLM) imaged onto the camera, the method further comprising:

splitting light from the laser into the input light and reference light both having a frequency of the light;

modulating, using a modulator, the reference light with a signal frequency, wherein the signals also have the signal frequency and modulate the input light with the signal frequency to form the modulated light;

combining the reference light and the collected modulated light, such that the reference light and the collected modulated light interfere and form an interference pattern on the camera;

measuring the phase map of the collected modulated light using the interference pattern and a computer;

irradiating the scattering medium with time reversed light comprising the time reversed fields, wherein the reference light is guided to reflect off the SLM and the SLM modulates the reference light using the phase conjugate map to form the time reversed light;

modifying the phase conjugate map into a digitally manipulated phase conjugate map by the digital manipulation; and irradiating the scattering medium with background light comprising the background fields, wherein the reference light is guided to reflect off the SLM and the SLM modulates the reference light using the digitally manipulated phase conjugate map to form the background light.

5. The method of claim 4, wherein the digital manipulation comprises digitally shifting the phase conjugate map by a plurality of pixels of the SLM.

6. The method of claim 4, wherein the digital manipulation comprises dividing the phase conjugate map into sub-regions and phase-shifting every other sub-region by a plurality of degrees.

7. The method of claim 4, further comprising:

compensating for curvature of the SLM; and randomly alternating between at least two trigger delays between the light, comprising pulsed light, and the signals, comprising pulsed ultrasound waves, to counter a phase drift between a non-modulated background, comprising the input light passing through the one or more regions and that is not modulated, and the reference light, wherein the phase drift leads to an added artificial signal on the phase map.

8. The method of claim 2, wherein:

(a) the source of signals is an ultrasound transducer, (b) the scattering medium is supported in a holder, wherein the ultrasound transducer, the laser, and the holder are connected such that:
  (i) the ultrasound transducer transmits ultrasound waves to one or more foci in the one or more regions of the scattering medium;
  (ii) the laser transmits the input light to the foci in the one or more regions of the scattering medium concurrently with the ultrasound waves, and
  (iii) the ultrasound waves at least partially frequency shift the input light into the modulated light, as the input light passes through the foci concurrently with the ultrasound waves;

(c) the SLM comprises a digital programmable SLM connected to and imaged onto a digital camera, wherein:
  (i) the camera is positioned to collect the portion of modulated light, and output one or more digital signals in response thereto;
  (ii) one or more computers connected to the DOPC device:
    (1) measure one or more phases of the collected modulated light using the digital signals; and
    (2) phase conjugate the phases to produce phase conjugate phases, and perform the modifying step by phase shifting one or more of the phase conjugate phases by one or more amounts to remove the desired component that converges to the foci;
  (ii) the SLM is programmed and positioned to modulate light into output light comprising the time reversed fields or the background fields; and
  (iv) the DOPC device is connected to the holder, wherein the DOPC device transmits the output light to the one or more foci.

9. The method of claim 2, wherein the modifying is in a computer connected to the DOPC device, and:

the camera comprises an analog/digital dynamic range of at least 16 bits;

the SLM comprises a resolution of at least 1920 by 1080 pixels and an input frame rate of at least 60 Hz;

the DOPC device outputs output light, comprising the time reversed fields, with a power having a gain of at least $10^5$ as compared to a power of the modulated light collected by the DOPC; and a response time is faster than 6.7 seconds, wherein the response time is a time between the encoding and the irradiating with the second output radiation that produces the second detected signal.

10. The method of claim 9, wherein the SLM and the camera are connected such that one SLM pixel is imaged onto one camera pixel.

11. The method of claim 2, wherein the scattering medium is biological tissue and the one or more regions are positioned at a depth of at least 2.5 millimeters below a surface of the biological tissue through which the input light enters the biological tissue.

12. The method of claim 2, wherein the signals comprise acoustic or ultrasound waves generated by an acoustic wave source.

13. The method of claim 12, wherein the ultrasound waves are generated by an ultrasound transducer and focused such that the one or more regions comprise one or more ultrasound foci of the ultrasound waves.

14. The method of claim 13, wherein the modifying and the foci are such that the output has a lateral resolution of at most 36 µm by 52 µm and an axial resolution of at most 657 µm.

15. The method of claim 2, wherein:
the irradiating with the time reversed fields and the background fields excites fluorescent agents in the one or more regions, thereby producing fluorescence; and
the method further comprises imaging the scattering medium using the fluorescence.

16. The method of claim 2, wherein the irradiating further comprises:
using the time reversed fields to excite fluorescent agents or photosensitizing agents in the one or more regions, wherein the excited fluorescent agents or photosensitizing agents induce biochemical reactions in the one or more regions of the scattering medium.

17. The method of claim 1, wherein the signals are ultrasound signals.

18. An apparatus for irradiating a scattering medium, comprising:
(a) an ultrasound transducer for transmitting ultrasound waves to one or more foci in one or more regions of a scattering medium;
(b) a laser for transmitting input light to the one or more foci, wherein the ultrasound waves at least partially frequency shift the input light into modulated light as the modulated light passes through the foci concurrently with the ultrasound waves;
(c) a Digital Optical Phase Conjugation (DOPC) device, comprising a digital programmable spatial light modulator (SLM) connected to and imaged onto a digital camera, wherein:
  (i) the camera:
    is positioned to collect a portion of the modulated light that has exited the scattering medium, as collected modulated light, and
    outputs one or more digital signals in response thereto;
  (ii) a computer connected to the DOPC device calculates one or more phases of the collected modulated light using the digital signals;
  (iii) a computer connected to the DOPC device computes phase conjugate phases that are phase conjugates of the phases of the collected modulated light;
  (iv) the DOPC device irradiates the scattering medium with time reversed fields having the phase conjugate phases, wherein the time reversed fields include a desired component that converges back to the foci, and a background component due to incomplete time reversal resulting from only the portion of the modulated light being collected;
  (v) a computer connected to the DOPC device phase shifts one or more of the phase conjugate phases by one or more amounts to remove the desired component that converges to the foci, to produce one or more background fields that at least approximate the background component;
  (vi) the SLM is programmed and positioned to sequentially modulate light to form first the light comprising time reversed fields and then the light comprising the background fields;
(d) a detector, wherein:
  the detector detects fluorescence transmitted from the scattering medium in response to the time reversed fields, to produce a first detected signal, and
  the detector detects fluorescence transmitted from the scattering medium in response to the background fields, to produce a second detected signal, and
(e) a computer connected to the detector, wherein the computer subtracts the second detected signal from the first detected signal, to obtain an output that at least approximates an interaction between a complete time reversed light field, comprising phase conjugates of all of the modulated light's fields, and the scattering medium.

19. The apparatus of claim 18, further comprising:
a first beam splitter positioned to split light from the laser, into the input light and reference light both having a frequency of the light;
a modulator positioned to modulate the reference light with an ultrasound frequency of the ultrasound waves, to form modulated reference light;
one or more second beam splitters, wherein one of the second beam splitters is positioned to combine the modulated reference light and the collected modulated light, such that the modulated reference light and the collected modulated light interfere and form an interference pattern on the camera; and wherein:
  the computer connected to the DOPC, that measures the one or more phases, computes a phase map of the collected modulated light using the interference pattern;
  the computer connected to the DOPC device, that computes the phase conjugate phases and the phase shifts, computes a phase conjugate map comprising phase conjugates of the phase map, and phase shifts by digitally manipulating the phase conjugate map to form a digitally manipulated phase conjugate map; and
one of the second beam splitters is positioned to guide the modulated reference light such that the modulated reference light reflects off the SLM, the SLM sequentially modulating the modulated reference light with the phase conjugate map and the digitally manipulated phase conjugate map, to irradiate the scattering medium first with the time reversed fields and then with the background fields.

20. The apparatus of claim 19, further comprising:
a computer connected to the laser and the ultrasound transducer, wherein the computer randomly alternates between at least two trigger delays between the light, comprising pulsed light, and the ultrasound waves, comprising pulsed ultrasound waves, to counter a phase drift between a non-modulated background comprising the input light, passing through the one or more regions and that is not modulated, and the reference light, wherein the phase drift leads to an added artificial signal on the phase map.

21. A method of fabricating an apparatus for irradiating a scattering medium, comprising:
  (a) providing, positioning, or providing and positioning, a source of one or more signals, such that the source transmits the one or more signals to one or more regions of a scattering medium;
  (b) providing, positioning, or providing and positioning, a laser, such that the laser transmits input electromagnetic (EM) radiation through the one or more regions of the scattering medium concurrently with the one or more signals, wherein the one or more signals at least partially modulate the input EM radiation into modulated radiation;
  (c) providing, positioning, or providing and positioning, a Digital Optical Phase Conjugation (DOPC) device such that the DOPC device collects at least a portion of the modulated radiation, that has exited the scattering medium, as collected modulated radiation; and
  (d) providing, connecting, or providing and connecting, one or more computers, such that the one or more computers:
    (i) receive a phase map of the collected modulated radiation,
    (ii) digitally phase conjugate the phase map to produce a phase conjugate map,
    (iii) digitally modify the phase conjugate map to produce a digitally modified phase map used to produce one or more background fields that at least approximate a background component, the background component resulting from incomplete time reversal of the modulated radiation, and the incomplete time reversal resulting from only the portion of the modulated radiation being collected;
    (iv) output the phase conjugate map and the digitally modified phase map to the DOPC device; and wherein the DOPC device:
      produces first EM radiation using the phase conjugate map, the first EM radiation including the background component and a desired component comprising time reversed EM radiation that converges back to the one or more regions, and the first EM radiation irradiating and interacting with the scattering medium to produce a first detected signal, and
      produces second EM radiation comprising the one or more background fields, using the digitally modified phase map, the second EM radiation irradiating and interacting with the scattering medium to produce a second detected signal; and
  the one or more computers subtract the second detected signal from the first detected signal to obtain an output that at least approximates an interaction between complete time reversed EM radiation, obtained by phase conjugating all the modulated radiation, and the scattering medium.

22. A method of irradiating a scattering medium, comprising:
  receiving a phase map of a portion of modulated radiation, wherein the portion of the modulated radiation was obtained from a process comprising:
    (i) modulating electromagnetic (EM) radiation with a signal, in a region of a scattering medium, to form the modulated radiation;
    (ii) collecting the portion of the modulated radiation in a digital optical phase conjugation (DOPC) device; and
    (iii) measuring the phase map of the portion of the modulated radiation;
  digitally phase conjugating the phase map to produce a phase conjugate map;
  digitally modifying the phase conjugate map to produce a digitally modified phase map used to produce one or more background fields that at least approximate a background component, the background component resulting from incomplete time reversal of the modulated radiation, and the incomplete time reversal resulting from only the portion of the modulated radiation being collected;
  outputting the phase conjugate map and the digitally modified phase map to the DOPC device;
  receiving a first detected signal and a second detected signal, wherein:
    the first detected signal was formed using a process comprising:
      producing first EM radiation, in the DOPC device, using the phase conjugate map, the first EM radiation including the background component and a desired component comprising time reversed EM radiation that converges back to the region, and the first EM radiation irradiating and interacting with the scattering medium to produce the first detected signal; and
    the second detected signal was formed using a process comprising:
      producing second EM radiation comprising the one or more background fields, in the DOPC device and using the digitally modified phase map, the second EM radiation irradiating and interacting with the scattering medium to produce the second detected signal;
  subtracting the second detected signal from the first detected signal to obtain an output that at least approximates an interaction between complete time reversed EM radiation, obtained by phase conjugating all the modulated radiation, and the scattering medium.

* * * * *